United States Patent
Kleiber et al.

(10) Patent No.: US 6,475,721 B2
(45) Date of Patent: *Nov. 5, 2002

(54) SEQUENCE SPECIFIC DETECTION OF NUCLEIC ACIDS USING A SOLID CARRIER BOUND WITH NUCLEIC ACID ANALOG PROBES

(75) Inventors: Jörg Kleiber, Penzberg (DE); Henrik Ørum, Vorlose (DE); Ane-Ullerup Lester, Narum (DK); Albert Geiger, Penzberg (DE)

(73) Assignee: Boston Probes, Inc., Bedford, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/894,808

(22) PCT Filed: Mar. 4, 1996

(86) PCT No.: PCT/EP96/00893
§ 371 (c)(1),
(2), (4) Date: Nov. 12, 1997

(87) PCT Pub. No.: WO96/27680
PCT Pub. Date: Sep. 12, 1996

(65) Prior Publication Data
US 2001/0010902 A1 Aug. 2, 2001

(30) Foreign Application Priority Data
Mar. 4, 1995 (EP) .............................. 95103122

(51) Int. Cl.$^7$ ............................ C12Q 1/68; C12P 19/34; C12M 1/34; C07H 21/04
(52) U.S. Cl. ............................. 435/6; 435/7.1; 435/91.1; 435/91.2; 435/287.1; 436/518; 436/527; 436/528; 436/536; 536/22.1; 536/23.1; 536/24.3; 536/24.33
(58) Field of Search ........................ 435/6, 91.1, 91.2, 435/283.1, 285.2, 287.1, 287.2; 536/24.3, 24.31; 436/518, 527, 528, 536; 546/105

(56) References Cited

U.S. PATENT DOCUMENTS

| | | | | |
|---|---|---|---|---|
| 5,217,866 A | * | 6/1993 | Summerton et al. | 435/6 |
| 5,412,087 A | * | 5/1995 | McGall et al. | 536/24.3 |
| 5,424,188 A | * | 6/1995 | Schneider et al. | 435/6 |
| 5,503,980 A | * | 4/1996 | Cantor et al. | 435/6 |
| 5,612,458 A | * | 3/1997 | Hyldig-Nielsen et al. | 530/388.21 |
| 5,631,134 A | | 5/1997 | Cantor et al. | |
| 5,648,213 A | * | 7/1997 | Reddy et al. | 435/6 |
| 6,015,902 A | * | 1/2000 | Bieniarz et al. | 546/105 |
| 6,387,163 B1 | * | 3/2002 | Buchardt et al. | 435/6 |

FOREIGN PATENT DOCUMENTS

EP 0 742 287 A2 11/1996
WO WO92/20703 * 11/1992

OTHER PUBLICATIONS

Chong et al Post Hybridization recovery of membrane filter-bound DNA for enzymatic DNA amplification. bio Techniques vol. (14) No. 4 575–579,578.*
Mann et al Two hour DNA hybridizations using a new transfer membrane Nucleic Acids Res. vol. 17(13) pp. 5410 1989.*
Southern et al Genomics 13, pp. 1008–1017,1992.*
Maskos et al Nucleic Acids Research vol. 20, No. 7, pp. 1675–1678, 1992.*
Guo et al Nucleic Acids Research vol. 22, No. 24 pp. 5456–5465, 1994.*
Egholm et al Nature vol. 365 pp. 566–568, 1993.*
Nielsen et al Science vol. 254 pp1497–500, 1991.*
International Publication No. WO 92/20702 published Nov. 26, 1992.
International Publication No WO 93/25706 published Dec. 23, 1993.
International Publication No. WO 89/10977 published Nov. 16, 1989.
International Publication No. WO 89/11548 published Nov. 30, 1989.
International Publication No. WO 97/05276 published Feb. 13, 1997.
International Publication No. WO 89/11545 published Nov. 30, 1989.
International Publication No. WO 95/01370 published Jan. 12, 1995.
Thonnard et al, Clinical Chemistry, 41/4, 533–556 (1995), "HLA Class II Genotyping: Two Assay Systems Compared".
Egholm et al, Nature, vol. 365, Oct. 7, 1993, "PNA hybridizes to complementary oligonucleotides obeying the Watson–Crick hydrogen–bonding rules".
Ørum et al, Nucleic Acids Research, 1993, vol. 21, No. 23, "Single base pair mutation analysis by PNA directed PCR clamping".
Beattie et al, Clin. Chem. 41/5, 700–706(1995), "Advances in Genosensor Research".
Guo et al, Nucleic Acids Research, 1994, vol. 22, No. 24, "Direct fluorescence analysis of genetic polymorphisms by hybridization with oligonucleotide arrays on glass supports".
Sidransky et al, Science, vol. 256, Apr. 3, 1997, "Identification of ras Oncogene Mutations in the Stool of Patients with Curable Colorectal Tumors".
Saiki et al, Proc. Natl. Acad. USA., vol. 86, pp. 6230–6234, Aug. 1989, "Genetic analysis of amplified DNA with immobilized sequence–specific olignucleotide probes".

* cited by examiner

Primary Examiner—Jeffrey Siew
(74) Attorney, Agent, or Firm—Arent Fox Kintner Plotkin & Kahn, PLLC

(57) ABSTRACT

A method for the detection of point mutation and polymorphisms in nucleic acids or for sequencing of unknown nucleic acids by a simple procedure using arrays uses nucleic acid analoges as sequence discriminators. This procedure simplifies the working mode in complex problematic cases.

41 Claims, 8 Drawing Sheets

|  |  | SEQ.ID.NO |
|---|---|---|
| H-ado$_3$-TGT ACG TCA CAA CTA -Gly-NH$_2$ | PNA 1a | 7 |
| H-ado$_6$-TGT ACG TCA CAA CTA -Gly-NH$_2$ | PNA 1b | 1 |
| H-ado$_9$-TGT ACG TCA CAA CTA -Gly-NH$_2$ | PNA 1c | 9 |
| H-ado$_6$-TGT ACG TGA CAA CTA -Gly-NH$_2$ | PNA 2 | 2 |
| H-ado$_6$-TGT ACA TCA CAA CTA -Gly-NH$_2$ | PNA 3 | 3 |

FIG. 1a

| 5'-(T)$_{15}$ TGT ACG TCA CAA CTA -3' | DNA 1 | 8 |
|---|---|---|
| 5'-(T)$_{15}$ TGT ACG TGA CAA CTA-3' | DNA 2 | 10 |
| 5'-(T)$_{15}$ TGT ACA TCA CAA CTA-3' | DNA 3 | 11 |

FIG. 1b

| Dig-5'-TAG TTG TGA CGT ACA -3' | ODN 1a | 4 |
|---|---|---|
| $^{32}$P-5'-TAG TTG TGA CGT ACA -3' | ODN 1b | 4 |
| Dig-5'-TAG TTG TCA CGT ACA -3' | ODN 2 | 5 |
| Dig-5'-TAG TTG TGA TGT ACA -3' | ODN 3 | 6 |

FIG. 1c

| | |
|---|---|
| H-ado$_6$- TGT ACG TCA CAA CTA -Gly-NH$_2$ | PNA 1 |
| 3'- ACA TGC AGT GTT GAT-5'-Dig | ODN 1 |
| | |
| H-ado$_6$- TGT ACG TGA CAA CTA -Gly-NH$_2$ | PNA 2 |
| 3'- ACA TGC AGT GTT GAT-5'-Dig | ODN 1 |
| | |
| H-ado$_6$- TGT ACA TCA CAA CTA -Gly-NH$_2$ | PNA 3 |
| 3'- ACA TGC AGT GTT GAT-5'-Dig | ODN 1 |
| | |
| H-ado$_6$- TGT ACG TCA CAA CTA -Gly-NH$_2$ | PNA 1 |
| 3'- ACA TGC ACT GTT GAT-5'-Dig | ODN 2 |
| | |
| H-ado$_6$- TGT ACG TGA CAA CTA -Gly-NH$_2$ | PNA 2 |
| 3'- ACA TGC ACT GTT GAT-5'-Dig | ODN 2 |
| | |
| H-ado$_6$- TGT ACA TCA CAA CTA -Gly-NH$_2$ | PNA 3 |
| 3'- ACA TGC ACT GTT GAT-5'-Dig | ODN 2 |
| | |
| H-ado$_6$- TGT ACG TCA CAA CTA -Gly-NH$_2$ | PNA 1 |
| 3'- ACA TGT AGT GTT GAT-5'-Dig | ODN 3 |
| | |
| H-ado$_6$- TGT ACG TGA CAA CTA -Gly-NH$_2$ | PNA 2 |
| 3'- ACA TGT AGT GTT GAT-5'-Dig | ODN 3 |
| | |
| H-ado$_6$- TGT ACA TCA CAA CTA -Gly-NH$_2$ | PNA 3 |
| 3'- ACA TGT AGT GTT GAT-5'-Dig | ODN 3 |

FIG. 1d

1nM ODN 1:
PNA 1
PNA 2 (G/G)
PNA 3 (A/C)

1nM ODN 2:
PNA 1 (C/C)
PNA 2
PNA 3 (A/C, C/C)

1nM ODN 3:
PNA 1 (G/T)
PNA 2 (G/T, G/G)
PNA 3

I  control experiment, ODN 1a (1pMol, 1nM), line 1 (PNA1), line 2 (PNA2) line 3 (PNA3)

II  ss amplificate (118bp, single DIG-labeled)
5 min. heat denaturation at 94°C
(50μl PCR-mixture diluted in 1ml hybridisation buffer)
line 1 (PNA1), line 2 (PNA2) line 3 (PNA3)

III  ds amplificate (118bp, single DIG-labeled)
(50μl PCR-mixture directly diluted in 1ml hybridisation buffer)
line 1 (PNA1), line 2 (PNA2) line 3 (PNA3)

1 5 10 20 40 100 pmol PNA 1 5 10 20 40 100 pmol PNA

SEQUENCE SPECIFIC DETECTION OF NUCLEIC ACIDS USING A SOLID CARRIER BOUND WITH NUCLEIC ACID ANALOG PROBES

Subject matter of the invention is a solid carrier having two or more nucleic acid analogs with different base sequences bound to predetermined sites on its surface. The invention also addresses a method for the detection of nucleic acids using a carrier of this nature.

Sample analysis has undergone rapid development in recent decades. While analytes were initially detected primarily by means of their reaction with conventional chemical reagents, and later on with enzymes, tests that utilize the immunological characteristics of the analyte have become the standard recently, especially in medical diagnostics. This is especially true in the field of infectious diseases. However, immunological procedures can basically only detect analytes with which immunologically active compounds such as antigens or antibodies play a role. These procedures have resulted in promising potential applications for many infections caused by viruses or bacteria. Genetic diseases or predispositions that are not expressed as a change in protein patterns—or only to an insufficient extent—are either difficult or impossible to detect using immunological procedures, however. Nucleic acids have therefore recently become the object of detection in many cases. The presence of certain nucleic acids can infer the presence of an infectious agent or the genetic condition of an organism. Detection procedures based on the presence of special nucleotide sequences in particular were facilitated recently when methods for the amplification of nucleic acids that are present in small numbers became available. Due to the large quantity of sequence information and the fact that two nucleotide sequences with completely different functions often differ by just one base unit, the specific detection of nucleotide sequences still poses a considerable challenge for reagents and analytical methods that are based on the detection of nucleic acid sequences. In addition, the nucleotide sequences are often not even known, but rather are determined for the first time in the nucleic acid detection method itself.

A method for the detection of nucleotide sequences of the HLA gene is described in EP-B-0 237 362 with which a clinically relevant point mutation can be detected. In this method, an oligonucleotide that is bound to a membrane and has a nucleotide sequence that is exactly complementary to one of the two nucleic acids to be differentiated is brought in contact with the sample. While certain conditions are maintained, only that nucleic acid that is exactly complementary binds to the oligonucleotide that is bound to the solid phase, and can be detected.

A method is described in Proc. Natl. Acad. Sci. USA 86, 6230–6234 (1989) in which a large number of oligonucleotides that are bound to different, predetermined sites of a nylon membrane by means of poly-dT are used for the simultaneous detection of all known allelic variants of an amplified region of a nucleic acid.

A method is described in U.S. Pat. No. 5,202,231 in which the sequence of a nucleic acid can be determined theoretically by bringing oligonucleotides having a predetermined, known sequence in contact with a sample of the unknown nucleic acids under hybridization conditions. This requires that all possible permutations of the nucleotide sequence be immobilized on known sites of a solid phase. By determining the sites to which the nucleic acids containing the sequence to be determined hybridize, it can theoretically be determined which sequences are present in the nucleic acid.

Prior art in the field of the analysis of genetic polymorphisms using "oligonucleotide arrays" is described in Nucleic Acids Research 22, 5456–5465 (1994) and Clin. Chem. 41/5, 700–6 (1995).

The main problem with the prior art is the fact that the melting temperatures of the selected sequence-specific oligonucleotides containing the nucleic acids to be sequenced or detected are different. To remedy this situation, one has to perform the complex method of selecting the length of the oligonucleotide and its base composition, and optimizing the position of the mismatches within the oligonucleotide as well as the salt concentration of the hybridization complex. In many cases, however, it is practically impossible to simultaneously distinguish closely related sequences from each other. The hybridization temperature is another critical parameter. Variations of as little as 1 to 2° C. can change the intensity or produce false-negative results. Incorrect analytical results based on the presence of point mutations have serious implications for diagnosis.

The object of this invention was, therefore, to provide an alternative method for the sequence-specific detection of nucleic acids and to provide suitable materials for this method.

This object was accomplished by providing a solid carrier having two or more nucleic acid analogs with different base sequences bound to predetermined sites on its surface. Another object of the invention is a method for the sequence-specific detection of a nucleic acid using this solid carrier.

A "solid carrier" as described by this invention refers to an object that has a surface that is so broad that specific areas can be distinguished upon it. This surface is preferably flat and larger than 5 $mm^2$, and is preferably between 10 $mm^2$ and approx. 100 $cm^2$. The carrier material is not liquid or gaseous, and preferably dissolves either not at all or incompletely in the sample fluids or reaction preparations that are used to immobilize nucleic acids to the surface. Examples of such materials are glass, plastics (e.g. polystyrene, polyamide, polyethylene, polypropylene), gold, etc. The material does not necessarily have to be completely solid itself, but rather can be made solid by the attachment of supporting materials.

The external shape of the solid carrier basically depends on the method used to detect the presence of nucleic acids on this solid carrier. It has proven to be appropriate, for instance, to select a basically planar form, e.g. a chip. Solid carriers that are especially suitable are, therefore, polystyrene chips that are from 1 to 5 mm thick and have a surface area of from 1 to 5 $cm^2$, for instance. Polyamide membranes that are 4×2.5 $cm^2$ in size have proven to be especially well-suited for use with this invention. Two or more nucleic acid analogs having different base sequences are bound to different sites of the surface of this carrier. These sites or regions preferably do not overlap with each other. They are preferably separated from each other by regions on the surface to which no nucleic acid analogs are bound. The sites to which the nucleic acid analogs are bound are referred to as "binding regions" below. The binding regions can have different shapes. These shapes are basically determined by the method of manufacturing the solid carrier or by the method used to determine the nucleic acid analogs in the binding regions. The minimum size of the binding regions is basically determined by the instrument with which the event—the binding of a nucleic acid to nucleic acid analogs of a region—is detected. Instruments are already available that can detect binding to regions that are approx. 1 mm in size. The upper limit of the size of the binding regions is determined by cost effectiveness and handling considerations.

The size of the binding regions is also basically determined by the methods used to apply the nucleic acid analogs to the surface. Such methods will be described later.

The number of binding regions on the solid carrier depends on the intended use of the solid carrier. In the simplest case, just two binding regions are needed to detect a certain point mutation. In this case, a binding region contains nucleic acid analogs that have a base in the position at which the point mutation is to be detected. This base is complementary to the base in the position of the normal sequence. The other binding region, on the other hand, contains a nucleic acid analog that has a base in the corresponding position that is complementary to the base of the mutated sequence. In another case, two nucleic acids or nucleic acid sequences that are only slightly related to each other can be detected simultaneously using a solid carrier that has two completely different nucleic acid analogs bound to its surface.

"Nucleic acid analogs" refer to non-naturally occurring molecules that can detect nucleic acids by means of base pairings. They therefore contain a specific base sequence that is completely complementary to the base sequence of a nucleic acid to be detected. The base sequence is therefore preferably composed of two naturally occurring nucleobases. As long as the specificity of the base pairing is not lost, modifications to the nucleobases are also allowed, however.

Those nucleic acid analogs are considered complementary to a nucleic acid that have a base sequence that forms hydrogen bridges with a base sequence of the nucleic acid per the principle of base pairing when it is bound to the nucleic acid. This sequence is preferably at least 8 bases long and, more preferably, between 8 and 25 bases long.

The nucleic acid analogs are further defined by the fact that they are structurally different from nucleic acids, at least in terms of the backbone. The "backbone" in nucleic acids or a nucleic acid analog refers to a structure that is basically composed of identical units that each contain a base. In naturally occurring nucleic acids, the backbone is a sugar phosphate backbone. This backbone is structurally modified in nucleic acid analogs, e.g. in that the sugar or phosphate portion is completely or partially replaced with other chemical units such as non-cyclic components. Basically, identical units can also replace each other in the backbone.

A few characteristics of nucleic acid analogs are described below to facilitate the selection of nucleic acid analogs that are suitable for use with this invention. It is advantageous for nucleic acid analogs to have a higher affinity to sequence-complementary nucleic acids than an oligonucleotide with an identical base sequence. In addition, those nucleic acid analogs are preferred that carry fewer charges than a corresponding oligonucleotide of the same length, or that can compensate charges with the opposite charges. Basically, uncharged nucleic acid analogs are especially preferred. Especially preferred nucleic acid analogs are those whose affinity to complementary nucleic acids basically does not depend on the salt content of the hybridization complex.

The nucleic acid analogues that are especially suitable are the nucleic acid analogs described in WO 92/20702 and WO 92/20703 (*Peptide Nucleic Acid,* PNA, e.g. *Nature* 365, 566–568 (1993) and *Nucl. Acids Res.* 21, 5332–5 (1993)). These patent applications are referred to for the description of the structure of the nucleic acid analogs. In preferred embodiments, the nucleic acid analogs used in the invention have the general formula (I):

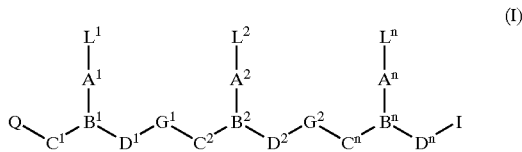

wherein:

n is at least 2, each of $L^1$–$L^n$ is independently selected from the group consisting of hydrogen, hydroxy, ($C_1$–$C_4$) alkanoyl, naturally occurring nucleobases, non-naturally occurring nucleobases, aromatic moieties, DNA intercalators, nucleobase-binding groups and reporter ligands, at least one of $L^1$–$L^n$ being a naturally occurring nucleobase, a non-naturally occurring nucleobase, a DNA intercalator, or a nucleobase-binding group;

each of $A^1$ through $A^n$ is a single bond, a methylene group or a group of formula (IIa) or (IIb):

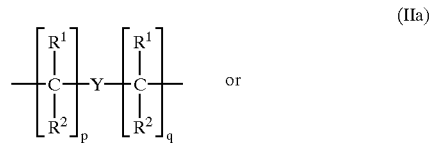

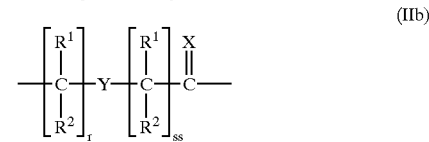

wherein in (IIa) or (IIb);

X is O, S, Se, $NR^3$, $CH_2$ or $C(CH_3)_2$;

Y is a single bond, O, S or $NR^4$;

each of p and q is an integer from 1 to 5, the sum p+q being not more than 10;

each of r and ss is zero or an integer from 1 to 5, the sum r+ss being not more than 10;

each $R^1$ and $R^2$ is independently selected from the group consisting of hydrogen, ($C_1$–$C_4$) alkyl which may be hydroxy- or alkoxy- or alkylthio-substituted, hydroxy, alkoxy, alkylthio, amino and halogen; and each $R^3$ and $R^4$ is independently selected from the group consisting of hydrogen, ($C_1$–$C_4$) alkyl, hydroxy- or alkoxy- or alkylthio-substituted ($C_1$–$C_4$) alkyl, hydroxy, alkoxy, alkylthio and amino;

and wherein in formula (I)

each of $B^1$–$B^n$ is N or $R^3N^+$, where $R^3$ is as defined above;

each of $C^1$–$C^n$ is $CR^6R^7$, $CHR^6CHR^7$ or $CR^6R^7CH_2$, wherein $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$) alkyl, aryl, aralkyl, heteroaryl, hydroxy, ($C_1$–$C_6$) alkoxy, ($C_1$–$C_6$) alkylthio, $NR^3R^4$ and $SR^5$, where $R^3$ and $R^4$ are as defined above, and $R^5$ is hydrogen, ($C_1$–$C_6$) alkyl, hydroxy-, alkoxy-, or alkylthio- substituted ($C_1$–$C_6$) alkyl, or $R^6$ and $R^7$ taken together complete an alicyclic or heterocyclic system;

each of $D^1$–$D^n$ is $CR^6R^7$, $CH_2CR^6R^7$ or $CHR^6CHR^7$, where $R^6$ and $R^7$ are as defined above;

each of $G^1$–$G^{n-1}$ is

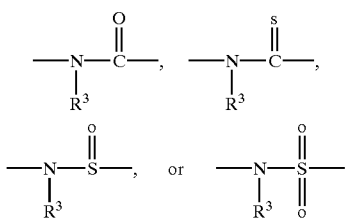

in either orientation, wherein $R^3$ is as defined above;

Q is —$CO_2H$, —$CONR'R''$, —$SO_3H$ or $SO_2NR'R''$ or an activated derivative of —$CO_2H$, —$SO_3H$; and I is —$NHR'''R''''$ or —$NR'''C(O)R''''$, where R', R'', R''' and R'''' are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers. Alternatively, C and D may be $CHR^6(CH_2)_{sss}CHR^7$ where sss may be from 0 to 2.

Preferred peptide nucleic acids have general formula (III):

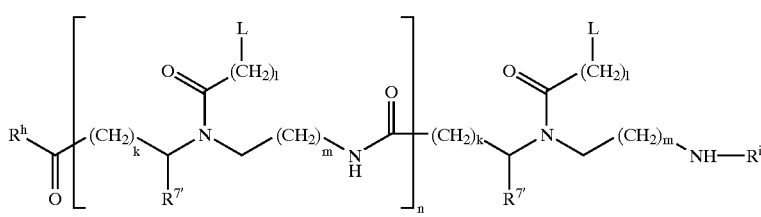

(III)

wherein:
each L is independently selected from the group consisting of hydrogen, phenyl, heterocycles, e.g. of one, two or three rings, naturally occurring nucleobases, and non-naturally occurring nucleobases;
each $R^{7'}$ is independently selected from the group consisting of hydrogen and the side chains of naturally occurring alpha amino acids;
n is an integer from 1 to 60;
each of k, l and m is independently zero or an integer from 1 to 5; preferably the sum of k and m is 1 or 2, most preferably 1;
$R^h$ is OH, $NH_2$, or —$NHLysNH_2$; and
$R^i$ is H or $COCH_3$.

Particularly preferred are compounds having formula (III) wherein each L is independently selected from the group consisting of the nucleobases thymine (T), adenine (A), cytosine (C), guanine (G) and uracil (U), in particular thymine, and n is an integer from 1 to 30, in particular from 4 to 20. An example of such a compound is provided in FIG. 1, which shows the structural similarity between such compounds and single-stranded DNA.

Preferred nucleic acid analogs are compounds that have a polyamide backbone that contains a number of bases bound along the backbone, with each base bound to a nitrogen atom of the backbone. Nucleic acid analogs should also include compounds, however, like those described in EP-A-0 672 677. Additional nucleic acid analogs are described in Recueil 91, 1069 –1080 (1971), *Method in Molecular Biology* 29, 355–389 (1983), *Tetrahedron* 31, 73–75 (1975), *J. Org. Chem.* 52, 4202–4206 (1987), *Nucl. Acids Res.* 17, 6129–6141 (1989), *Unusual Properties of New Polymers* (Springer Verlag 1983), 1–16, *Specialty Polymers* (Springer Verlag 1981), 1–51, WO 92/20823, WO 86/05518 and WO 86/05519. Additional nucleic acid analogs are described in *Proc. Natl. Acad. Sci. USA* 91,7864–7868 (1994), *Proc. Nat. Acad. Sci. USA* 92,6097–6101 (1995) and *J. Am. Chem. Soc.* 117, 6140–6141 (1995). The nucleic acid analogs described are from 8 to 30 bases long, while a length of from 10 to 25 bases is especially advantageous. The nucleic acid analogs named are bound directly or indirectly to the surface of the solid carrier. The type of binding basically depends on which reactive group are available for binding on the solid carrier, and which reactive groups are available for binding to the nucleic acid analog without restricting the ability of the nucleic acid analogs to bind to a complementary nucleic acid. The type of binding also depends on whether the intent is to simultaneously bind the nucleic analogs to different sites, or to build upon them. It can also be appropriate to cover the surface of the solid carrier with a layer of a material that has a great ability to bind, or to activate the surface by means of a chemical reaction. Reactive groups on the surface of a solid carrier are usually selected from the group —OH, —$NH_2$ and SH. Reactive groups of nucleic acid analogs are preferably selected from the group —OH, $NH_2$, —SH, —COOH, —$SO_3H$ and —$PO_3H_2$.

In an especially preferred embodiment, the reactive groups of the surface and the nucleic acid analog are covalently bound to each other, especially by means of a linker that is more than 15 atoms and less than 200 atoms long. A "linker" refers to a portion of a molecule that basically has the function of removing the nucleic acid analogs that are sterically available on the surface of the solid carrier. A linker is usually selected that has hydrogen atoms (e.g. in alkylene units) and numerous heteroatoms (e.g. —O— or —NH— or —NR—) that facilitate solvation. The linker preferably contains one or more ethylene oxy units and/or peptide groups. In an especially preferred embodiment, the linker contains one or more units as described in DE-A 3924705. Especially preferred are the units described as an example which is referred to as Ado (8-amino-3,6-dioxa-octanic acid), below. A slight dependence of the binding of nucleic acids to the PNA surface can be reduced by using longer linkers between PNA and the solid carrier.

The nucleic acid analog that is bound to a site can also be a mixture of two or more analogs having different but known sequences. This can reduce the number of sites required for a multiple determination.

The surface of the carrier is preferably not charged, and is preferably hydrophilic. The invention demonstrated that the use of basically uncharged surfaces is an advantage when detecting nucleic acids.

A solid carrier loaded with nucleic acid analogs at different sites as provided by this invention can be manufactured in different ways. In one embodiment, suitable quantities of solutions that each contain different nucleic acid analogs are applied to different sites on the surface of the solid carrier, e.g. via pipette. The liquid samples should not mix with each other on the surface of the solid carrier. This can be accomplished, for instance, by locating the application sites far apart from each other or by using a hydrophobic barrier to stop the expansion of the liquid between the various sites. Either the nucleic acid analogs or the surface of the solid carrier is preferably activated for the reaction. This activation can be achieved, for instance, in that one of the groups described above is activated by the creation of a reactive species. In the case of a carboxyl group, this would be an activated ester (e.g. a N-hydroxy succinimide ester) that quickly enters into an ester bond with a hydroxyl group without further activation. Suitably activated polyamide membranes carry triazine groups, for instance, that can react with amino groups of nucleic acid analogs with the formation of a covalent bond. The activation can also take place by means of bifunctional reagents, squaric acid derivatives of WO 95/15983 or glutaraldehyde (GB 2197720).

The binding of the analogs can also be realized by coating the carrier surface with nucleotide sequences that are complementary to a part of the sequence of the nucleotide analogs. The binding of the different nucleic acid analogs to the binding regions can take place simultaneously or sequentially.

After a sufficient amount of time has passed for the binding to take place, it is advantageous to wash away any nucleic acid analogs that have not bound or are bound insufficiently, along with any binding reagents that were used. This is performed preferably under conditions in which non-bound nucleic acid analogs cannot bind with nucleic acid analogs that are bound to other regions.

Basically, it is also possible to build upon the nucleic acid analogs on the different sites of the surface by means of monomeric units. The technology described in WO 92/10092 or WO 90/15070 can be used for this purpose. Appropriate monomers are described in WO 92/20702, for instance.

Another subject matter of this invention is a method for the sequence-specific detection of a nucleic acid using the solid carrier provided by this invention.

Detectable nucleic acids are natural or artificial nucleic acids. "Nucleic acids" therefore also refer to nucleic acid analogs. The nucleic acid to be detected, however, is the RNA or DNA in particular that is characteristic for an organism containing nucleic acids, e.g. a virus, a bacterium, a multicellular organism, a plasmid or a genetic condition such as a predisposition or a disposition for a certain disease or a spontaneous genetic mutation. The RNA and DNA in this case is basically of genomic origin or an origin derived therefrom. An important class of nucleic acids in the context of this invention are the results of a nucleic acid amplification. These results are also referred to as "amplificates" or "amplicons" below. The nucleic acids can be present in either their raw form or in a purified or processed form. A purification can also take place by separating the nucleic acids from cell components in a preparatory step, e.g. an affinity separation step. The nucleic acids can also be enzymatically extended, specifically amplified or transcribed.

For the sequence-specific detection of nucleic acids, the carrier provided by this invention has a nucleic acid analog bound to a site that has a base sequence that is complementary to a base sequence of the nucleic acid to be detected. This base sequence is selected intentionally so that it can specifically reveal the presence of the nucleic acid. In the normal case this means that the mixture contains as few as possible—and preferably no—additional nucleic acids having the same total sequence. It must be mentioned, however, that the carrier provided by this invention can also be used to specifically detect groups of nucleic acids. It can be a task of the method, for instance, to detect any member of a certain taxonomic group, e.g. a family of bacteria, by means of its nucleic acids. In this case, the base sequence of the nucleic acid analog can be intentionally selected so that it lies in a conserved region but only occurs in members of this taxonomic group.

An additional nucleic acid analog that has a base sequence that is not complementary to the same base sequence is preferably bound to a different site of the surface. It can be a nucleic acid analog, the base sequence of which can be shorter or longer, or which can differ from the first nucleic acid analog by one or more bases. The difference in the base sequence depends on the task to be solved. The differences can include point mutations, or smaller deletions and insertions, for instance. In many genetic diseases, such as cystic fibrosis, the sequences of the nucleic acid analogs differ in terms of individual positions (point mutations) and numerous positions (deletions, for example at Δ508).

The mutation to be detected is preferably positioned close to the middle of the base sequence of the analog.

The sequences of the analog can also be intentionally selected so that their hybridization positions differ by one base each, even though the lengths are identical (overlap). The sequences can also be intentionally selected so that the hybridization regions are adjacent to each other on the nucleic acid to be detected.

Numerous mutations can also be detected in the same or different nucleic acids by selecting nucleic acid analogs with sequences that are complementary to the sequence on these nucleic acids.

In an especially easy case in which the purpose is to determine which of two alleles is present in a complex, two nucleic acid analogs are bound to different sites of the surface of the solid carrier, the base sequences of which differ in exactly that position where the alleles also differ. A nucleic acid analog is therefore selected that is complementary to a certain sequence of one allele, while the other nucleic acid analog is complementary to the sequence of the other allele. The length and hybridization sites of the nucleic acid analogs are identical.

All alleles are usually detected for cystic fibrosis, for instance. The wild-type contains two healthy alleles. Heterozygotes contain one mutated and one wild-type sequence, and homozygotic mutants contain two mutant nucleic acids. In this case, the intent is not just to determine if mutants are present, but to determine if it is a heterozygotic or homozygotic case. In accordance with this invention it is possible to simultaneously quantitatively detect both alleles and thereby differentiate between the three cases described.

In many cases, especially in oncology and in the determination of infectious parameters, mutated cells/particles are usually located in the background of non-mutated/normal cells. In these cases, selective detection can not be performed reliably or at all using methods provided by the state of the art. The analysis of ras mutations from DNA from stool samples, for instance, requires that a mutated sequence be reliably detected in the presence of approx. 100 normal sequences (Science 256, 102–105 (1992)). In the field of infectious diseases, it would be desirable to determine different HIV populations in one infected patient. The quantity of many mutants of these HIV populations is less than 2% compared with all HIV sequences, however. The method provided by this invention therefore makes it especially quite possible to investigate mixtures of nucleic acids that are very similar to each other, even if one of the nucleic acids is present in a much greater quantity than the nucleic acid to be determined.

The lengths of the bound nucleic acid analogs are preferably identical. An appropriate length has proven to be between 10 and 100, and preferably between 10 and 50 bases. Especially good results are obtained with nucleic acid analogs that are between 10 and 25 bases long.

To perform the method provided by this invention, the sample containing nucleic acid is brought in contact with the sites on the surface of the carrier that have bound the nucleic acid analogs. This can be performed, for instance, by bringing the solid carrier into the sample fluid or pouring the sample fluid onto the solid carrier in one or more portions. The nucleic acids in the sample fluid can be denatured (single-strand) before they are brought in contact with the carrier. A major advantage of the invention, however, is the fact that a preliminary denaturation step can be eliminated, e.g. by using PNAs. The PNAs force a strand out of the double-stranded nucleic acid to be determined. The only important requirement is that the sample be brought in contact with the solid carrier under conditions in which the nucleic acid to be detected binds specifically to the appropriate site on the surface by means of the nucleic acid analog which is complementary to one sequence of the nucleic acid to be determined. These conditions can be different for different types of nucleic acid analogs, of course, but they are easily determined for given nucleic acid analogs by performing tests. In the normal case, these conditions are based on the conditions that are known for carriers loaded with oligonucleotides. If nucleic acid analogs are used as described in WO 92/20702, however, conditions can be selected that are much different from the hybridization conditions for the corresponding oligonucleotides. It has proven to be appropriate, however, to use much less salt than when the corresponding oligonucleotides are used. For instance, the presence of less than 100 mM and, more preferably, less than 50 mM, and most preferably, less than 10 mM salt is recommended. Under these conditions, it would not be possible to sufficiently differentiate between nucleic acids having similar sequences using oligonucleotides having the same sequence.

The sample is kept in contact with the surface as long as necessary to achieve a sufficient binding of the nucleic acids to the appropriate site on the surface. This period is usually a few minutes.

In the next step, it is determined whether the nucleic acid has bound to the surface and, if so, to which site. This is considered an indication of the presence of a nucleic acid that contains a base sequence that is complementary to the nucleic acid analog bound to this site. The binding can be determined using various methods.

Instruments are already available with which changes on specific sites of surfaces can be determined directly. For methods that use these types of instruments it is not even necessary to remove the sample containing the nucleic acid from the surface after it has been applied. Normally, however, it is preferable to remove the fluid from the surface and use a wash solution to remove any remaining reagent that is still adhered to the surface. This step provides the advantage of also washing away sample components that can interfere with the determination of the binding.

In a preferred embodiment, the binding of the nucleic acid to be detected with the nucleic acid analog is determined by means of a label that is inserted in the nucleic acid to be determined in a step that is performed before the sample is brought in contact with the surface. The label can be a detectable group such as a fluorescent group, for instance. This determination can be performed optically using a microscope or in a measuring cell provided for this purpose. While the site at which the binding took place is an indication of the presence of a nucleic acid having a certain sequence, the quantity of label at a predetermined site can be used as an indication of the quantity of the nucleic acid to be determined.

In an especially preferred embodiment, the nucleic acids to be detected are the products of a nucleic acid amplification method such as the polymerase chain reaction as described in EP-B-0 202 362, or NASBA as described in EP-A-0 329 822. It is important that the nucleic acid sequence to bind with the nucleic acid analog be amplified by the amplification method. The better the amplification method maintains the original sequence—that is, the fewer errors that are incorporated into the sequence during amplification—the more suitable the amplification method. The polymerase chain reaction has proven to be especially suitable. The amplification primers are selected specifically so that the nucleic acid sequence to be detected lies in the region between the hybridization sites.

It has also proven advantageous to insert the label required for the detection reaction into the amplificate during amplification. This can be performed, for instance, by using labelled primers or labelled mononucleoside triphosphates.

The binding that took place can be detected directly without inserting a label, for instance, by using an intercalating agent. These agents have the characteristic of depositing selectively on double-stranded compounds that contain bases, including the complex of the nucleic acid analog and the nucleic acid bound in sequence-specific fashion. The presence of the complexes can be detected using specific characteristics of intercalating agents, e.g. fluorescence. Ethidium bromide is an especially suitable agent.

Another method for detecting hybrids without inserting a label is based on surface plasmon resonance, as described in EP-A-0 618 441, for instance.

According to another possible method for determining the binding, the surface is brought in contact with a solution of an antibody labelled for detection. This antibody is directed against the complex consisting of the nucleic acid analog and the nucleic acid to be determined. Antibodies of this nature are described in WO 95/17430, for instance.

The detection of the hybrids depends on the type of labelling used. The hybrids can be detected with a scanner, a CCD camera or a microscope, for instance.

This invention provides numerous advantages. In particular, it allows detecting sequence differences in nucleic acid regions located within secondary structures. With this invention it is also possible to increase the sensitivity of detection, because it can use a greater absolute quantity of bound nucleic acid to be determined than traditional methods. It is also possible, in particular, to increase the signal-to-noise ratio compared with methods that use oligonucleotides. In the first attempt, a signal-to-noise ratio of less than 1:1000 was obtained.

The invention can be used in at least two fields. In the first case, the solid carrier is used to detect known mutations and polymorphisms. In this case, the number of mutations and polymorphisms to be determined is an indicator of the number of different nucleic acid analogs or sites required on the surface. The sequence of the nucleic acid analogs is specially coordinated with the sequence of the nucleic acids around the mutations and polymorphisms. Preferably, the sequences are selected in such a way that the base by which nucleic acid analogs having similar sequences differ is located in or near the middle of the sequence.

The carriers provided by this invention can be used in the following fields:

Infectious diseases, the simultaneous determination of different analytes/parameters, and in investigations of the condition of a gene in a bacterium or virus, e.g. for multidrug resistance studies.

Oncology (detection of mutations in tumor suppressor genes and oncogenes, and in the determination of the relationship between mutated and normal cells).

Investigation of inherited diseases (cystic fibrosis, sickle cell anemia, etc.).

Tissue and bone marrow typing (MHC complex) (see Clin. Chem. 41/4, 553–5 (1995)).

In a second potential application, a sequence of short nucleic acid fragments can be determined using the method called "sequencing by hybridizatior". In this method, the same number of different nucleic acid analogs are immobilized as there are permutations of the selected length of the sequence. To achieve a sufficient level of sensitivity, $4^N$ sites are required, with N equal to the number of bases in each nucleic acid analog. Preferably, N is between 5 and 12. Correspondingly fewer sites are required to sequence very short DNA fragments. The method for sequencing unknown nucleic acids using the "sequencing by hybridization" method is described in WO 92/10588.

An advantage of this invention is the fact that the specificity of the hybridization is largely independent of the conditions in the sample. This facilitates simultaneous binding of nucleic acids to different regions on the surface.

Surprisingly, it was shown that nucleic acid analogs such as PNA have an excellent ability to discriminate between sequences on the surface. This discrimination was better than was to be expected from the melting temperatures of analogous, dissolved compounds.

Surprisingly, the carriers provided by this invention are even suitable for use in numerous, consecutive determinations of nucleic acids. After a determination is performed, the carrier that is in contact with a fluid undergoes heat treatment. A temperature is selected at which the bond between the nucleic acid analog and the nucleic acid is dissolved. The carrier is then available to perform another determination. With the method provided by this invention, it is possible for the first time to determine relative quantities of very similar nucleic acids located next to each other in a sample in a concentration range of at least two logs. It has been possible to quantitatively determine mutants using sequencing methods, for instance. The maximum level of discrimination available with this method was 1:10, however.

With the method provided by this invention it is also possible to bind double-stranded DNA to the immobilized nucleic acid analogs of the solid carrier without a denaturation step. Comparison studies have shown that this is not possible with immobilized DNA. It has also been shown that mismatches that are not located in the center of the hybrid can also be distinguished with a high degree of selectivity.

BRIEF DESCRIPTION OF THE DRAWINGS

The sequences of the PNA molecules are shown in FIG. 1a. They are used as examples to explain the method. The PNAs were prepared as described in WO 92/20702.

FIG. 1b shows the sequences of the DNA molecules that are homologous to the PNA sequences from FIG. 1a and that were used for the DNA/ODN hybridization experiments.

FIG. 1c shows the sequences of the complementary oligonucleotides (ODN) used that were labelled with digoxigenin on the 5'-phosphate end using the 5'-DIG End Labelling Kit (Boehringer Mannheim) and that were phosphorylated with polynucleotide kinase and $^{32}$-P-g-ATP 5'.

FIG. 1d shows the feasible combinations of oligonucleotide (ODN) and PNA for forming hybrids. Identical combinations apply for hybridizations between DNA probes (DNA, see FIG. 1b) and oligonucleotides (ODN, see FIG. 1c).

I Control experiment, ODN 1a (1 pMol, 1 nM), line I (PNA 1), line 2 (PNA 2) line 3 (PNA 3)

II ss Amplificate (118 bp, one-fold DIG-labelled) 5 min heat denaturation at 94° C. (50 ml PCR preparation diluted in 1 ml hybridization buffer) Line 1 (PNA 1), line 2 (PNA 2), line 3 (PNA 3)

III ds Amplificate (118 bp, one-fold DIG-labelled) (50 ml PCR preparation diluted directly in 1 ml hybridization buffer) Line 1 (PNA 1), line 2 (PNA 2), line 3 (PNA 3)

Figure 4:
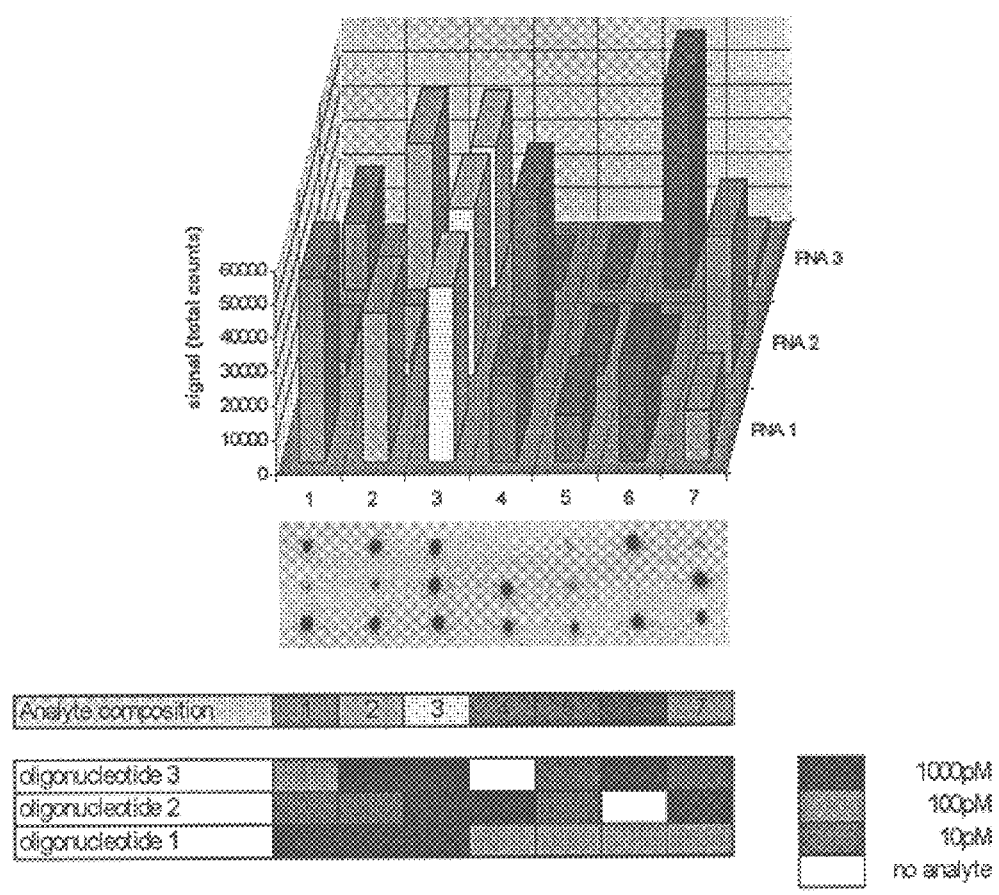

FIG. 4 shows the results of the qualitative and quantitative analysis of analyte mixtures by means of PNA arrays. The conditions were: 200 nl spot volume (100 mM PNA, one PNA per line, one analyte mixture per cleavage).

Figure 5:
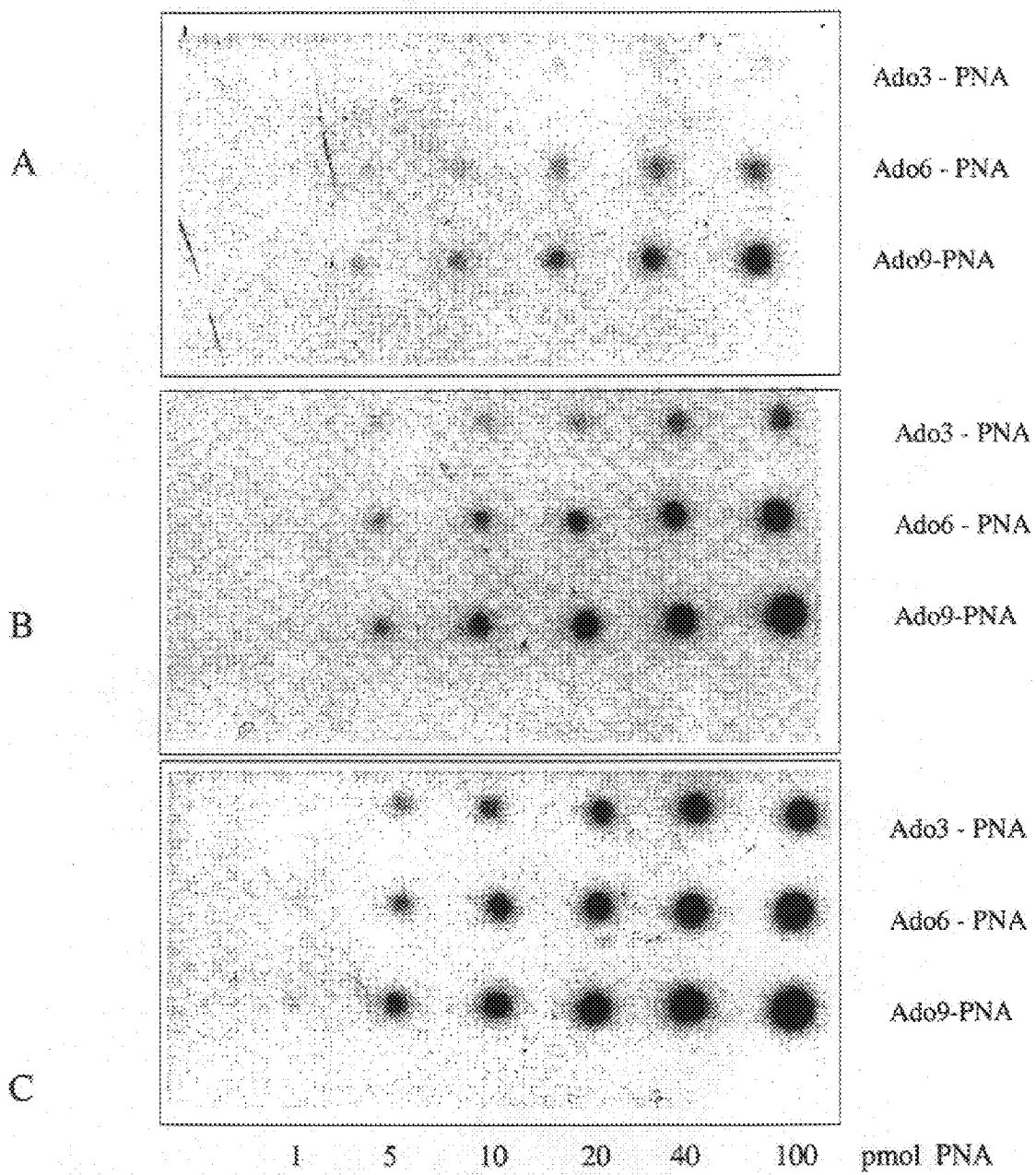

FIG. 5 shows the effect of linker length on the hybridization. The conditions were: 1 ml spot volume (100; 40; 20; 10; 5; 1 mM PNA, one concentration per cleavage, (Ado)$_3$-PNA in row 1, (Ado)$_6$-PNA in row 2, (Ado)$_9$-PNA in row 3). The labels in FIG. 5 mean:

A. Prehybridization/hybridization in 5 mM sodium phosphate, 0.1% SDS, pH 7.0

B. Prehybridization/hybridization in 10 mM sodium phosphate, 0.1% SDS, pH 7.0

C. Prehybridization/hybridization in 25 mM sodium phosphate, 0.1% SDS, pH 7.0

FIGS. 6a-6c demonstrate that PNA-derivatized membranes can be used many times after regeneration. The conditions were: 1 ml spot volume (100; 40; 20; 10; 5; 1 mM PNA, one concentration per cleavage).

Figure 6:
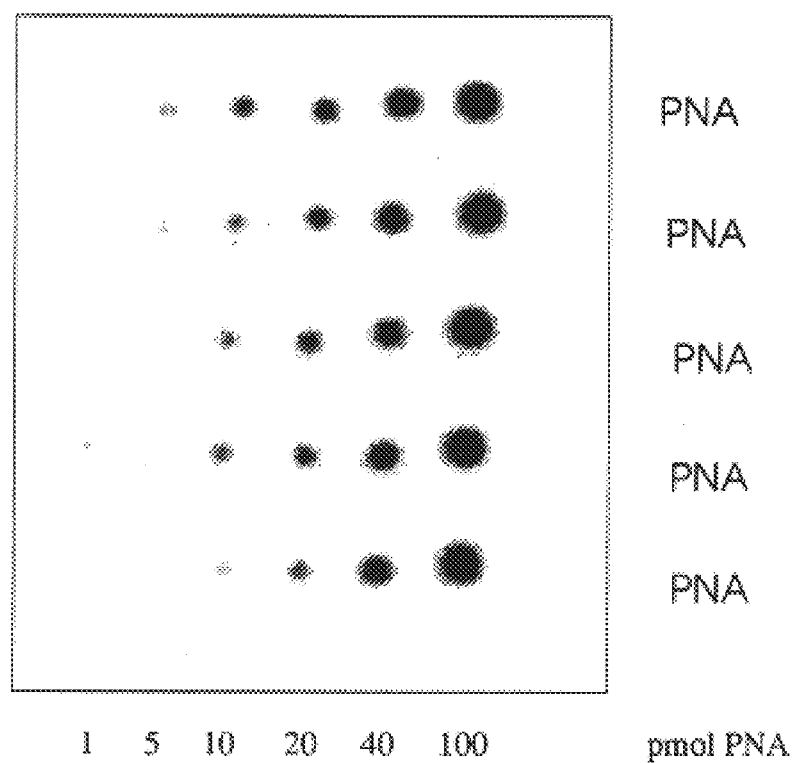
Figure 6:
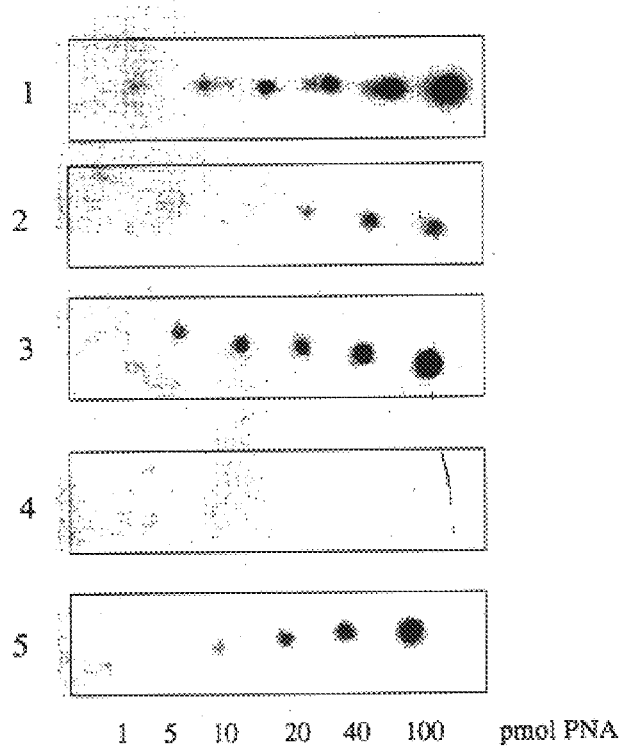
Figure 6:
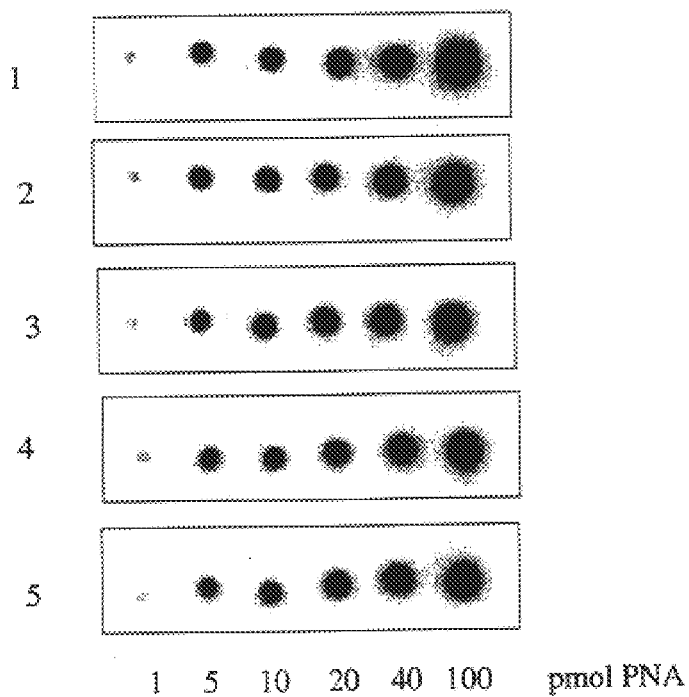

The labels in FIG. 6 mean:

6a: Signal intensities after the first hybridization

6b: Signal intensities after the regeneration procedure

Membrane 1: No regeneration (controls)

Membrane 2: Regeneration with 0.1 M sodium hydroxide solution, RT 1 h, 2×10 min bidistilled water RT Membrane 3: Regeneration with 1 M sodium hydroxide solution, RT, 1 h, 2×10 min bidistilled water RT Membrane 4: Regeneration with distilled water, 70° C. 1 h, 2×10 min bidistilled water RT Membrane 5: Regeneration with 0.1 M sodium hydroxide solution, 70° C. 1 h, 2×10 min bidistilled water RT 6c: Signal intensities after rehybridization This invention is explained in further detail using the following examples:

EXAMPLES

General

The nucleic acid analogs used were manufactured as described in WO 92/20702. Unless indicated otherwise, chemicals and reagents were products of Boehringer Mannheim GmbH.

Example 1

Covalent Derivatization of Nylon Membranes 200 nl of a solution that contains PNA in the desired concentration in 0.5 M sodium carbonate pH 9.0 are applied to an Immunodyne ABC membrane (Pall) with a pipette. After the spots are dry, the membrane is washed with 0.1 M sodium hydroxide solution to deactivate any reactive functional surface groups that may still be present. The membrane is washed a second time with water and then dried.

Example 2

Detection of a Hybridization Event Using Luminescence

The membrane is derivatized as described in Example 1 using 100 µM, 10 mM, 1 µM and 0.1 mM PNA solutions. It is then prehybridized in a 50 ml hybridization vessel with 10 ml hybridization buffer (10 mM sodium phosphate, pH 7.2, 0.1% SDS (sodium dodecylsulfate)) in a hybridization oven at 45° C. After 30 minutes, 10 ml of a solution that contains the DIG-labelled oligonucleotide in a 1 mM concentration is added and the complex is hybridized for another 60 minutes. It is then washed for 2×10 minutes with 25 ml wash buffer each time (5 mM sodium phosphate pH 7.2, 0.05% SDS) at 45° C. The detection reaction is performed according to the protocol for digoxigenin detection (DIG Detection Kit, Boehringer Mannheim GmbH, BRD). The anti-DIG-AP conjugate is used in a 1:10000 dilution. CDP-Star™ is used in a 1:10000 dilution as the substrate for the alkaline phosphatase.

Example 3

Detection of a Hybridization Event Using Fluorescence

The membrane is derivatized as described in Example 1 using 100 µM, 10 µM and 1 µM PNA solution. The membrane is prehybridized in a 50 ml screw-top container with 10 ml hybridization buffer (see Example 2) in the oven at 45° C. After 30 minutes, 10 ml of a solution that contains a fluorescent-labelled oligonucleotide in a concentration of 1 µM is added, and the preparation is hybridized for another 60 minutes. The membrane is then washed for 2×10 minutes with 25 ml wash buffer each time (see Example 2) at 45° C. The membrane is dried, then the intensity of the fluorescence is measured.

Example 4

Selectivity of the Method

Three membrane strips are derivatized with three (Ado)$_6$-PNA molecules each that differ according to one or two positions of their base sequence (see FIG. 1a, SEQ.ID.NOS. 1, 2, 3), using PNA solutions in a concentration range of between 100 mM and 0.1 mM as described in Example 1. The membrane strips are prehybridized with 10 ml hybridization buffer for 30 minutes in 50 ml screw-top containers. In the next step, one of the three DIG-labelled oligonucleotides (FIG. 1b, SEQ.ID.NOS. 4, 5, 6) is added. After hybridizing for 60 minutes, the membranes are washed for 2×10 minutes with 25 ml wash buffer each time. The hybridization events are detected as described in Example 2.

Figure 2:
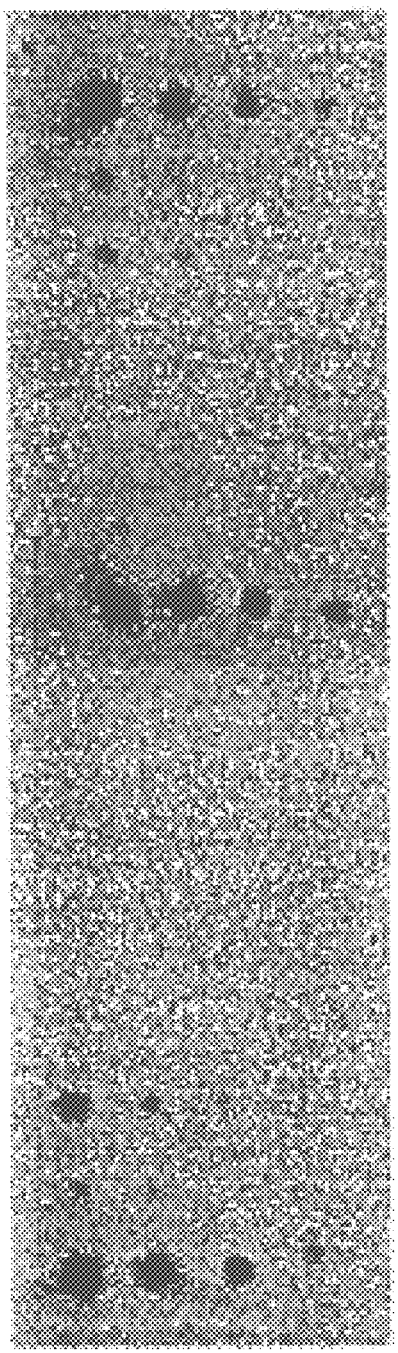
FIG. 2 shows the hybridization results from Example 4 to illustrate the selectivity of the method. The conditions were: 200 nl spot volume (100; 10; 1; 0.1 mM PNA, one concentration per cleavage), incubation at 45° C.

All possible double-stranded hybrids between the PNA molecules involved and the oligonucleotides are shown in FIG. 1d. FIG. 2 illustrates that, in almost every case, the only oligonucleotide detected is the one that is exactly complementary to the immobilized nucleic acid analog (PNA 1, PNA 2, PNA 3). The signal-to-noise ratios (S/N) can also be estimated from the figure. They were evaluated quantitatively, and the results are presented in Table 1.

TABLE 1

| Hybrid (PNA/ODN) | S/N | Signal (Hybrid)/Signal (Match) |
|---|---|---|
| 1/1 | 655.2 | 100.0% |
| 2/1 | 20.7 | 3.2% |
| 3/1 | 10.3 | 1.6% |
| 1/2 | 23.1 | 2.6% |
| 2/2 | 871.8 | 100.0% |
| 3/2 | 6.4 | 0.7% |
| 1/3 | 109.4 | 22.7% |
| 2/3 | 12.3 | 2.5% |
| 3/3 | 481.1 | 100.0% |

Example 5

Quantification

Membrane strips are derivatized with three (Ado)$_6$-PNA molecules with different base sequences (FIG. 1a, SEQ.ID.NOS. 1, 2, 3) in a concentration of 100 mM as described in Example 1. They are then prehybridized in 20 ml hybridization vessels with 10 ml hybridization buffer (see Example 2) at 45° C. The buffer is replaced after 30 minutes. In experiments 1 through 7, the buffer to be added differs according to the analyte concentrations of the DIG-labelled components—oligonucleotide 1, 2 and 3, SEQ.ID.NOS. 4, 5, 6. The strips are hybridized for 60 minutes at 45° C. and then washed for 2×10 minutes with 10 ml wash buffer. The detection is performed using the procedure described in Example 2. The luminescence signal is recorded with a luminescence imager and then evaluated (FIG. 4).

The signal intensities found can be used to reach a qualitative or semi-quantitative finding regarding the composition of the analyte complex. Absolutely quantitative findings can be reached after the signal intensities are calibrated.

Example 6

Detection of PCR Amplicons

A. Obtaining a Suitable Analyte (Amplificate)

A double-stranded DNA fragment is ligated in a pUC19 plasmid, the sequence of which is complementary to the PNA probe PNA 1. The plasmid is transformed in *E. coli*, cloned, and then sequenced. For the subsequent hybridization experiments, a section of the plasmid sequence is amplified and DIG-labelled during the amplification reaction. The amplification is performed in a total volume of 50 µl. The amplification complex consists of 1 µl plasmid (1 ng/µl) 1 µl primer F1 (10 µM), 1 µl DIG primer R1 (10 µM), 5 µl 10×PCR buffer (100 mM Tris/HCl, 15 mM MgCl$_2$, 500 mM KCl, pH 8.3), 2 µl dNTP solution (10 mM dATP, 10 mM dCTP, 10 mM dGTP, 10 mM dTTP in distilled water, pH 7.0), 0.5 µl Taq polymerase (5 units/µl) and 38.5 ml water.

Primer F1: 5'-GTA AAA CGA CGG CCA GT-3'    (SEQ.ID.NO. 12)
Primer R1: 5'-DIG-AAC AGC TAT GAC CAT GA-3'    (SEQ.ID.NO. 13)

Each reaction mixture is warmed to 96° C. for 3 minutes. In the next step, 30 rounds of a 3-level PCR cycle are performed (45 sec. 96° C., 30 sec, 48° C., 1 min 72° C.). In the last cycle, the elongation step is increased by 5 minutes at 72° C.

B. Hybridization Reaction

The membranes are derivatized with three $(Ado)_6$-PNA sequences each that differ according to one or two positions in their base sequence (see FIG. 1a, SEQ.ID.NOS. 1, 2, 3) using PNA solutions in a concentration range between 100 µM and 0.1 µM as described in Example 1. The membrane is pretreated in a 20 ml hybridization vessel with 5 ml hybridization buffer at 45° C. The buffer is replaced after 30 minutes and the analyte solution is added. To make the analyte solution, the amplification complex is diluted directly (ds amplicon) and, after 5 minutes of heat denaturation (ss amplicon), in 1 ml hybridization buffer. After hybridization for 1 h, 2 h 30 min and 4 h at 45° C., the membranes are washed for 2×10 minutes with 5 ml wash buffer each time. Hybridization events are detected as described in Example 2 (FIG. 3).

Figure 3:
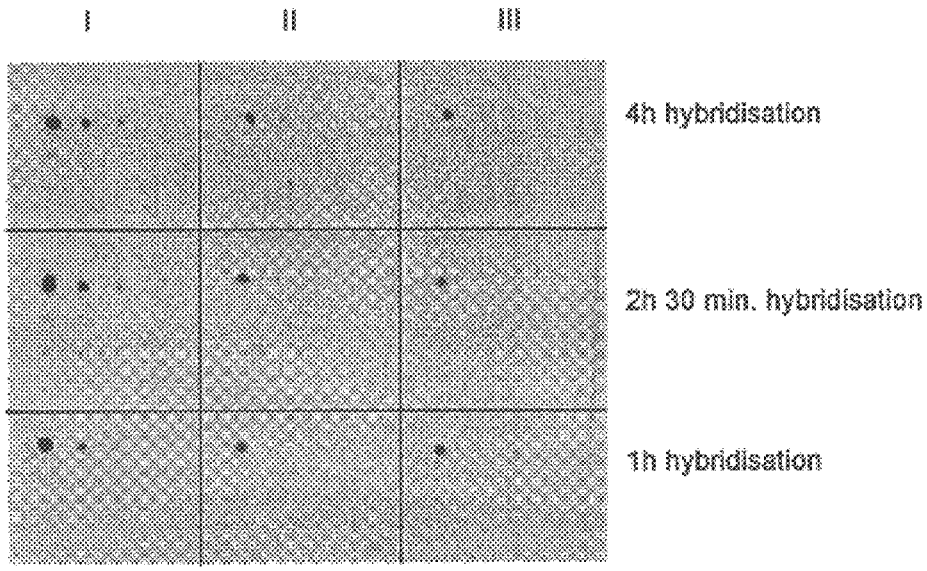
FIG. 3 shows the hybridization results from Example 6. They verify that PCR amplicons are detected by immobilized PNA probes. The conditions were: 200 nl spot volume (100; 10; 1; 0.1 mM PNA, one concentration per cleavage), incubation at 45° C. The labels in FIG. 3 mean.

Nine fields are shown in FIG. 3. The difference between each row is the incubation period (4 h, 2½ h, and 1 h). The difference between each column is the type of nucleic acid to be detected. Three overlapping rows of spots are applied to each of the 3 fields of column I. The difference between the rows is the sequence of the PNAs, while the difference between the columns of each field is the concentration. The specificity and the ability to be quantified are indicated in column I for the case in which oligonucleotides are used as the detecting nucleic acid.

The figure illustrates the influence of incubation time. It is clear that an excellent sequence discrimination for ODN 1a and the amplificates is obtained after hybridization for just one hour. The difference between columns II and III in FIG. 3 is that an amplificate that was previously made single-stranded is used in one case as the nucleic acid to be detected. In column III, an amplificate that was not previously made single-stranded is used as the nucleic acid to be detected. The signals indicate clearly that it is not necessary to denature double-stranded nucleic acids before applying them to the solid carrier. This decreases the number of working steps (heating step, single strand separation, wash step) and, therefore, reduces the danger of contamination. PNA probes in combination with low-salt conditions therefore offer clear advantages over DNA probes.

Example 7

Comparison of PNA/DNA Hybridization

Membrane strips are derivatized with three $(Ado)_6$-PNA sequences each (SEQ.ID.NOS. 1, 2, 3) and three DNA molecules each (SEQ.ID.NOS. 8, 10, 11) that differ according to one or two positions in their base sequence (see FIG. 1a and 1b) using 50 mM solutions as described in Example 1. Unlike Example 1, the spot volume is 400 nl instead of 200 nl. The membrane strips are prehybridized in 20 ml hybridization vessels with either 5 ml low-salt buffer (see Example 2) or high-salt buffer (6×SSC; 0.9 M NaCl, 90 mM sodium citrate, 0.1% SDS, pH 7.0) at either 37° C. or 45° C. for 30 minutes. In the next step, one of the three DIG-labelled oligonucleotides (FIG. 1c, SEQ.ID.NOS. 4, 5, 6) is added. After a hybridization step of 60 minutes, the strips are washed for 2×10 minutes with 5 ml wash buffer each time at 37° C. or 45° C. The wash buffer from Example 2 is used for the low-salt experiments. For the high-salt experiments, a 1×SSC buffer with 0.02% SDS, pH 7.0 is used. The hybridization results are detected as described in Example 2. The evaluation is performed quantitatively and is illustrated in Table 2.

Both the DNA and PNA probes are able to completely discriminate between complementary, single-stranded target sequences of single and double mismatched sequences. PNA probes demonstrate clear advantages over the DNA probes for certain types of mismatches, especially when they are not located in the middle of the sequence, but rather shifted to the end. This becomes especially clear in the example of a decentral G/T mismatch (probe 1/ODN 3), which is tolerated by the DNA probe much more strongly than by the PNA probe having the identical sequence.

TABLE 2

|  |  | PNA or DNA 1 | PNA or DNA 2 | PNA or DNA 3 |
|---|---|---|---|---|
| ODN 1 | PNA 45° C., low salt | 100.0% | 1.2% | 1.5% |
|  | DNA 37° C., high salt | 100.0% | 1.2% | 6.4% |
| ODN 2 | PNA 45° C., low salt | 1.1% | 100.0% | 2.9% |
|  | DNA 37° C., high salt | <2%* | 100.0% | <2%* |
| ODN 3 | PNA 45° C., low salt | 26.0% | 1.5% | 100.0% |
|  | DNA 37° C., high salt | 66.5% | <2%* | 100.0% |

*A more exact value cannot be determined because the spot intensity is lower than the standard deviation of the background signal.

Example 8

Influence of the Length of the Linker Between the Membrane and PNA Probes

Membrane strips are derivatized with PNA molecules (see FIG. 1a, SEQ.ID.NOS. 7, 1, 9) that differ according to the length of the linker ($Ado_3$, Ado6 or $Ado_9$) using PNA solutions in the concentration range between 100 µM and 1 µM as described in Example 1. Unlike Example 1, the spot volume is 1 µl instead of 200 nl. The membrane strips are prehybridized in hybridization containers with 10 ml hybridization buffer (5, 10 or 25 mM sodium phosphate, 0.1% SDS, pH 7.0) for 30 minutes at 35° C. In the next step, 10 pMol $^{32}$P-labelled oligonucleotide (see FIG. 1c: ODN 1b, SEQ.ID.NO. 4) is added and the preparation is hybridized for 60 minutes at 50° C. The membranes are washed for 2×10 minutes with 50 ml wash buffer (5 mM sodium phosphate, 0.1% SDS, pH 7.0) at 50° C. The hybridization events are detected using autoradiography (FIG. 5). The figure shows that a longer linker greatly improves the hybridization.

Example 9

Reuse of PNA Membranes

A membrane is derivatized with $(Ado)_6$-PNA molecules (see FIG. 1a: PNA 1b, SEQ.ID.NO. 1) using PNA solutions in a concentration range between 100 µM and 1 µM as described in Example 1. The PNA is applied in five identical concentration sequences. The spot volume is 1 µl, as in Example 8. The membrane is prehybridized in a hybridization vessel with 10 ml hybridization buffer (10 mM sodium phosphate, 0.1% SDS, pH 7.0) for 30 minutes at 35° C. In the next step, 10 pMol $^{32}$P-labelled oligonucleotide (see FIG. 1c: ODN 1b, SEQ.ID.NO. 4) is added and the preparation is hybridized for 60 minutes at 50° C. The membrane is washed for 2×10 minutes with 50 ml wash buffer (5 mM sodium phosphate, 0.1% SDS, pH 7.0) at 50° C. The hybridization events are detected using autoradiography (FIG. 6a). After the autoradiography is performed, the membrane is cut into five identical strips. These membrane strips are each treated differently in the rest of the experiment. Membrane 1 is not incubated and serves as the control membrane. Membrane 2 is incubated for 60 minutes at room temperature with 50 ml 0.1 M sodium hydroxide solution. Membrane 3 is incubated for 60 minutes as well, with 50 ml 1 M sodium hydroxide solution. Membrane 4 is incubated for 60 minutes at 70° C. with 50 ml distilled water. Membrane 5 is incubated for 60 minutes at 70° C. with 50 ml 0.1 N sodium hydroxide solution. All membranes are then washed with distilled water for 2×10 minutes. After this procedure is completed, autoradiography is performed once more (FIG. 6b). These membrane strips are then used a second time in a hybridization reaction as described, and the hybridization events are detected using autoradiography (FIG. 6c).

As shown in FIG. 6b, the different treatment methods yield very different results. Treatment with bidistilled water at 70° C. (membrane 4) causes the membrane to regenerate almost completely. An unexpected discovery was the fact that the success of the regeneration is poorer if conditions are used that are common for the denaturation of nucleic acids. As such, the incubation of membrane 3 with 1 M sodium hydroxide solution at room temperature yields virtually no regeneration effect. Decreasing the concentration of sodium hydroxide solution from 1 M to 0.1 M increases the degree of regeneration at room temperature (membrane 2) and at 70° C. (membrane 5). None of these conditions, however, results in an even slightly good degree of regeneration, as is the case with bidistilled water (membrane 4). The example shows that these conditions are important parameters for the efficient denaturation of membrane-bound PNA/DNA double-strands.

Regardless of the regeneration method, all membranes can be reused for hybridization (FIG. 6c), without considerably worsening the signal-to-noise ratio. Up to 6 rehybridizations could be performed without a noticeable effect on the PNA membranes' ability to regenerate or rehybridize.

What is claimed is:

1. A method for determining the location of two or more different peptide nucleic acid/nucleic acid complexes on a basically planar solid carrier, said method comprising:

treating the carrier with an agent that deposits selectively on the complexes; and determining the location of the agent on said carrier to thereby determine the location of the two or more complexes on said carrier.

2. The method of claim 1, wherein the agent is an intercalating agent.

3. The method of claim 1, wherein the agent is a detectably labeled antibody to the peptide nucleic acid/nucleic acid complex.

4. A method for the sequence-specific determination of mutations or polymorphisms in a nucleic acid, said method comprising:

contacting a sample that contains the nucleic acid to be determined with a basically planar solid carrier comprising at least two single stranded peptide nucleic acid probes of different base sequence covalently bound to said solid carrier, and wherein at least one peptide nucleic acid probe binds to nucleic acid in said sample under conditions where the nucleic acid to be determined in said sample binds to the peptide nucleic acid probe, and wherein at least one of said peptide nucleic acid probes has a base sequence that is complementary to the base sequence of the nucleic acid to be determined, and wherein at least one additional peptide nucleic acid probe has a base sequence that is not complementary to the base sequence of the nucleic acid to be determined, and determining in which region the nucleic acid to be determined binds to the peptide nucleic acid probes that are bound to said carrier, as an indication of the mutation or polymorphism of the nucleic acid to be determined; wherein the probes are nucleic acid analogs that have the general formula (I):

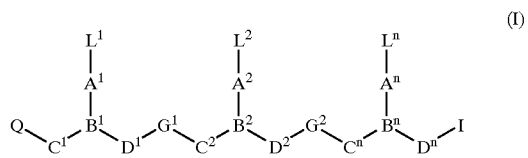

wherein:

n is at least 2, each of L¹–Lⁿ is independently selected from the group consisting of hydrogen, hydroxy, (C₁–C₄) alkanoyl, naturally occurring nucleobases, non-naturally occurring nucleobases, aromatic moieties, DNA intercalators, nucleobase-binding groups and reporter ligands, at least one of L¹–Lⁿ being a naturally occurring nucleobase, a non-naturally occurring nucleobase, a DNA intercalator, or a nucleobase-binding group;

each of A¹ through Aⁿ is a single bond, a methylene group or a group of formula (IIa) or (IIb):

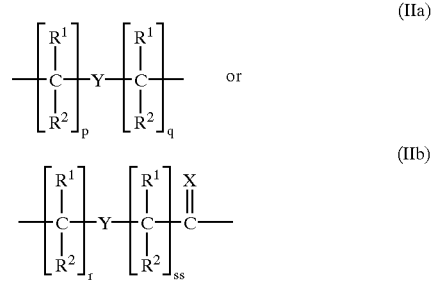

wherein in (IIa) or (IIb):

X is O, S, Se, NR³, CH₂ or C(CH₃)₂;

Y is a single bond, O, S or NR⁴;

each of p and q is an integer from 1 to 5, the sum p+q being not more than 10;

each of r and ss is zero or an integer from 1 to 5, the sum r+ss being not more than 10;

each R¹ and R² is independently selected from the group consisting of hydrogen, (C₁–C₄) alkyl which may be hydroxy- or alkoxy- or alkylthio-substituted, hydroxy, alkoxy, alkylthio, amino and halogen; and each R³ and R⁴ is independently selected from the group consisting of hydrogen, (C₁–C₄) alkyl, hydroxy- or alkoxy- or alkylthio-substituted (C₁–C₄)alkyl, hydroxy, alkoxy, alkylthio and amino;

and wherein in formula (I);

each of B¹–Bⁿ is N or R³N⁺, where R³ is as defined above;

each of C¹–Cⁿ is CR⁶R⁷, CHR⁶CHR⁷ or CR⁶R⁷CH₂, wherein R⁶ is hydrogen and R⁷ is selected from the group consisting of the side chains of naturally occurring alpha amino acids, or R⁶ and R⁷ are independently selected from the group consisting of hydrogen, (C₂–C₆) alkyl, aryl, aralkyl, heteroaryl, hydroxy, (C₁–C₆) alkoxy, (C₁–C₆) alkylthio, NR³R⁴ and SR⁵, where R³ and R⁴ are as defined above, and R⁵ is hydrogen, (C₁–C₆) alkyl, hydroxy-, alkoxy-, or alkylthio- substituted (C₁–C₆) alkyl, or R⁶ and R⁷ taken together complete an alicyclic or heterocyclic system;

each of D¹–Dⁿ is CR⁶R⁷, CH₂CR⁶R⁷ or CHR⁶CHR⁷, where R⁶ and R⁷ are as defined above;

each of G¹–Gⁿ⁻¹ is

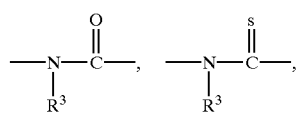

-continued

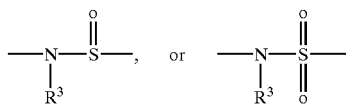

in either orientation, wherein R³ is as defined above;

Q is —CO₂H, —CONR'R", —SO₃H or SO₂NR'R" or an activated derivative of —CO₂H, —SO₃H; and I is —NHR'"R"" or —NR'"C(O)R"", where R', R", R'" and R"" are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers, wherein C and D can optionally be CHR⁶(CH₂)ₛₛₛCHR⁷ where sss is from 0 to 2.

5. The method according to claim 4, wherein the conditions under which the nucleic acid to be determined binds to the peptide nucleic acid probe include the presence of less than 100 mM salts.

6. The method according to claim 4, wherein the nucleic acid to be determined is produced by a nucleic acid amplification reaction.

7. The method according to claim 4, wherein the nucleic acid to be determined is detectably labeled.

8. The method according to claim, wherein the binding of the nucleic acid to the peptide nucleic acid probe is determined by using an intercalating agent.

9. The method according to claim 4, wherein a detectably labeled antibody to the nucleic acid/peptide nucleic acid binding complex is used to determine the binding of the nucleic acid to the peptide nucleic acid probe.

10. The method according to claim 4, wherein said nucleic acid is not denatured prior to contact with said solid carrier.

11. The method according to claim 4, wherein said nucleic acid is double stranded DNA that is not denatured prior to contact with said solid carrier.

12. The method of claim 4 wherein the peptide nucleic acids have a backbone of 2-aminoethyl-glycine subunits.

13. A method for the selective detection of nucleic acid mutants, said method comprising:

contacting a sample containing mutant nucleic acid, in the presence of a large amount of non-mutant nucleic acid, with a basically planar solid carrier comprising at least two single stranded peptide nucleic acid probes of different base sequence, each probe being covalently bound to a separate and distinct region of the solid carrier, and wherein at least one peptide nucleic acid probe binds to nucleic acid in said sample under conditions where nucleic acid binds to the peptide nucleic acid probe; and determining in the regions where the nucleic acid mutants, the non-mutant nucleic acids or both the nucleic acid mutants and the non-mutant nucleic acids bind to said solid carrier wherein the probes are nucleic acid analogs that have the general formula (I):

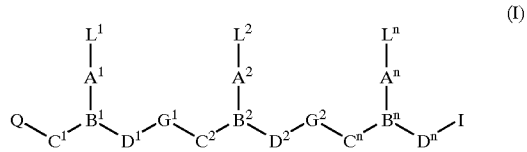

wherein:

n is at least 2, each of $L^1-L^n$ is independently selected from the group consisting of hydrogen, hydroxy, $(C_1-C_4)$ alkanoyl, naturally occurring nucleobases, non-naturally occurring nucleobases, aromatic moieties, DNA intercalators, nucleobase-binding groups and reporter ligands, at least one of $L^1-L^n$ being a naturally occurring nucleobase, a non-naturally occurring nucleobase, a DNA intercalator, or a nucleobase-binding group;

each of $A^1$ through $A^n$ is a single bond, a methylene group or a group of formula (IIa) or (IIb):

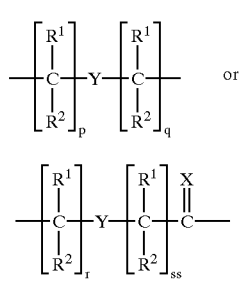

wherein in (IIa) or (IIb):
X is O, S, Se, $NR^3$, $CH_2$ or $C(CH_3)_2$;
Y is a single bond, O, S or $NR^4$;
each of p and q is an integer from 1 to 5, the sum p+q being not more than 10;
each of r and ss is zero or an integer from 1 to 5, the sum r+ss being not more than 10;
each $R^1$ and $R^2$ is independently selected from the group consisting of hydrogen, $(C_1-C_4)$ alkyl which may be hydroxy- or alkoxy- or alkylthio-substituted, hydroxy, alkoxy, alkylthio, amino and halogen; and
each $R^3$ and $R^4$ is independently selected from the group consisting of hydrogen, $(C_1-C_4)$ alkyl, hydroxy- or alkoxy- or alkylthio-substituted $(C_1-C_4)$alkyl, hydroxy, alkoxy, alkylthio and amino;
and wherein in formula (I);
each of $B^1-B^n$ is N or $R^3N^+$, where $R^3$ is as defined above;
each of $C^1-C^n$ is $CR^6R^7$, $CHR^6CHR^7$ or $CR^6R^7CH_2$, wherein $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$ alkyl, aryl, aralkyl, heteroaryl, hydroxy, $(C_1-C_6)$ alkoxy, $(C_1-C_6)$ alkylthio, $NR^3R^4$ and $SR^5$, where $R^3$ and $R^4$ are as defined above, and $R^5$ is hydrogen, $(C_1-C_6)$ alkyl, hydroxy-, alkoxy-, or alkylthio- substituted $(C_1-C_6)$ alkyl, or $R^6$ and $R^7$ taken together complete an alicyclic or heterocyclic system;
each of $D^1-D^n$ is $CR^6R^7$, $CH_2CR^6R^7$ or $CHR^6CHR^7$, where $R^6$ and $R^7$ are as defined above;

each of $G^1-G^{n-1}$ is

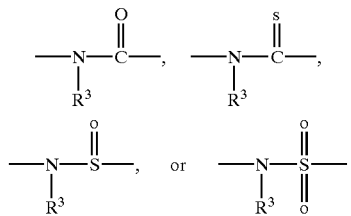

in either orientation, wherein $R^3$ is as defined above;

Q is $—CO_2H$, $—CONR'R''$, $—SO_3H$ or $SO_2NR'R''$ or an activated derivative of $—CO_2H$, $—SO_3H$; and I is $—NHR'''R''''$ or $—NR'''C(O)R''''$, where R', R'', R''' and R'''' are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers, wherein C and D can optionally be $CHR^6(CH_2)_{sss}CHR^7$ where sss is from 0 to 2.

14. The method according to claim 13, wherein the conditions under which the mutant and non-mutant nucleic acid binds to the peptide nucleic acid probes include the presence of less than 100 mM salts.

15. The method according to claim 13, wherein the amount of bound mutant and non-mutant nucleic acid bound to the solid carrier is determined by using an intercalating agent.

16. The method according to claim 13, wherein a detectably labeled antibody to the nucleic acid/peptide nucleic acid binding complex is used to determine the binding of mutant and non-mutant nucleic acid to the solid carrier.

17. The method of claim 13, wherein said peptide nucleic acids have the general formula (III):

(III)

wherein:
each L is independently selected from the group consisting of hydrogen, phenyl, heterocycles, one, two or three rings, naturally occurring nucleobases, and non-naturally occurring nucleobases;
each $R^{7'}$ is independently selected from the group consisting of hydrogen and the side chains of naturally occurring alpha amino acids;
n is an integer from 1 to 60;

each of k, l and m is independently zero or an integer from 1 to 5; and optionally the sum of k and m is 1 or 2;

$R^h$ is OH, $NH_2$ or —$NHLysNH_2$; and $R^i$ is H or $COCH_3$.

18. The method of claim 13 wherein the peptide nucleic acids have a backbone of 2-aminoethyl-glycine subunits.

19. A method for determining the relative amounts of a mutant nucleic acid and a non-mutant nucleic acid in a sample, said method comprising:

contacting a nucleic acid-containing sample with a basically planar solid carrier comprising at least two single stranded peptide nucleic acid probes of different base sequence, each probe being covalently bound to a separate and distinct region of the solid carrier, and wherein at least two peptide nucleic acid probes each bind to different nucleic acids in said sample under conditions where nucleic acid binds to the peptide nucleic acid probe; and determining the relative amount of mutant and non-mutant nucleic acid in said sample by comparing the amount of the mutant nucleic acid with the amount of the non-mutant nucleic acid, each being bound at different regions of the solid carrier wherein the probes are nucleic acid analogs that have the general formula (I):

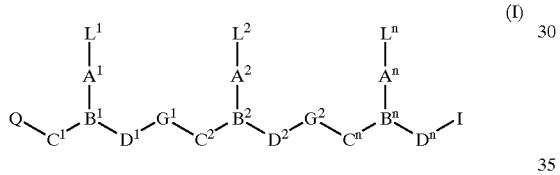

(I)

wherein:

n is at least 2, each of $L^1$–$L^n$ is independently selected from the group consisting of hydrogen, hydroxy, ($C_1$–$C_4$) alkanoyl, naturally occurring nucleobases, non-naturally occurring nucleobases, aromatic moieties, DNA intercalators, nucleobase-binding groups and reporter ligands, at least one of $L^1$–$L^n$ being a naturally occurring nucleobase, a non-naturally occurring nucleobase, a DNA intercalator, or a nucleobase-binding group;

each of $A^1$ through $A^n$ is a single bond, a methylene group or a group of formula (IIa) or (IIb):

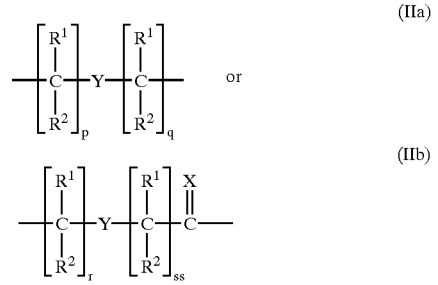

wherein in (IIa) or (IIb):

X is O, S, Se, $NR^3$, $CH_2$ or $C(CH_3)_2$;

Y is a single bond, O, S or $NR^4$;

each of p and q is an integer from 1 to 5, the sum p+q being not more than 10;

each of r and ss is zero or an integer from 1 to 5, the sum r+ss being not more than 10;

each $R^1$ and $R^2$ is independently selected from the group consisting of hydrogen, ($C_1$–$C_4$) alkyl which may be hydroxy- or alkoxy- or alkylthio-substituted, hydroxy, alkoxy, alkylthio, amino and halogen; and each $R^3$ and $R^4$ is independently selected from the group consisting of hydrogen, ($C_1$–$C_4$) alkyl, hydroxy- or alkoxy- or alkylthio-substituted ($C_1$–$C_4$)alkyl, hydroxy, alkoxy, alkylthio and amino;

and wherein in formula (I);

each of $B^1$–$B^n$ is N or $R^3N^+$, where $R^3$ is as defined above;

each of $C^1$–$C^n$ is $CR^6R^7$, $CHR^6CHR^7$ or $CR^6R^7CH_2$, wherein $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$) alkyl, aryl, aralkyl, heteroaryl, hydroxy, ($C_1$–$C_6$) alkoxy, ($C_1$–$C_6$) alkylthio, $NR^3R^4$ and $SR^5$, where $R^3$ and $R^4$ are as defined above, and $R^5$ is hydrogen, ($C_1$–$C_6$) alkyl, hydroxy-, alkoxy-, or alkylthio- substituted ($C_1$–$C_6$) alkyl, or $R^6$ and $R^7$ taken together complete an alicyclic or heterocyclic system;

each of $D^1$–$D^n$ is $CR^6R^7$, $CH_2CR^6R^7$ or $CHR^6CHR^7$, where $R^6$ and $R^7$ are as defined above;

each of $G^1$–$G^{n-1}$ is

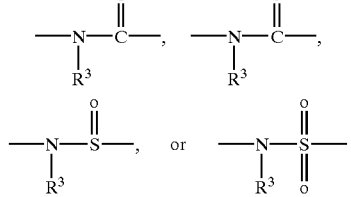

in either orientation, wherein $R^3$ is as defined above;

Q is —$CO_2H$, —CONR'R", —$SO_3H$ or $SO_2NR'R"$ or an activated derivative of —$CO_2H$, —$SO_3H$; and I is —NHR'"R"" or —NR'"C(O)R"", where R', R", R'" and R"" are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers, wherein C and D can optionally be $CHR^6(CH_2)_{sss}CHR^7$ where sss is from 0 to 2.

20. The method according to claim 19, wherein the conditions under which the mutant and non-mutant nucleic acid binds to the peptide nucleic acid probes include the presence of less than 100 mM salts.

21. The method according to claim 19, wherein the amount of bound mutant and non-mutant nucleic acid bound to the solid carrier is determined by using an intercalating agent.

22. The method according to claim 19, wherein a detectably labeled antibody to the nucleic acid/peptide nucleic acid binding complex is used to determine the binding of mutant and non-mutant nucleic acid to the solid carrier.

23. The method of claim 19, wherein said peptide nucleic acids have the general formula (III):

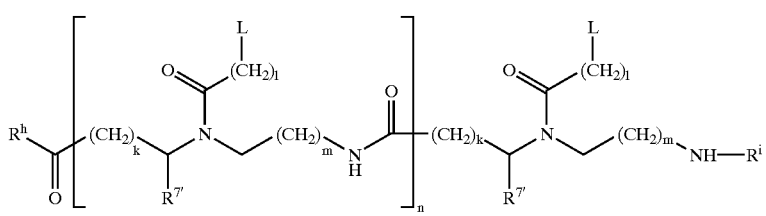

(III)

wherein:
each L is independently selected from the group consisting of hydrogen, phenyl, heterocycles, one, two or three rings, naturally occurring nucleobases, and non-naturally occurring nucleobases;
each $R^{7\prime}$ is independently selected from the group consisting of hydrogen and the side chains of naturally occurring alpha amino acids;
n is an integer from 1 to 60;
each of k, l and m is independently zero or an integer from 1 to 5; and optionally the sum of k and m is 1 or 2;
$R^h$ is OH, $NH_2$ or —$NHLysNH_2$; and
$R^i$ is H or $COCH_3$.

24. The method of claim 19 wherein the peptide nucleic acids have a backbone of 2-aminoethyl-glycine subunits.

25. A method for sequencing a nucleic acid, said method comprising:
contacting a nucleic acid-containing sample with a basically planar solid carrier comprising at least four single stranded peptide nucleic acid probes of different base sequence, each probe being covalently bound to a separate and distinct region of the basically planar solid carrier, and wherein at least one of the peptide nucleic acid probes each bind to different nucleic acids in said sample under conditions where the nucleic acid binds to the peptide nucleic acid probes and wherein the number of peptide nucleic acid probes bound to the solid carrier is equal to $4^N$, wherein N is the number of bases in each nucleic acid analogue; and
determining the region of the carrier to which the nucleic acid binds as an indication of the sequence of the nucleic acid wherein the probes are nucleic acid analogs that have the general formula (I):

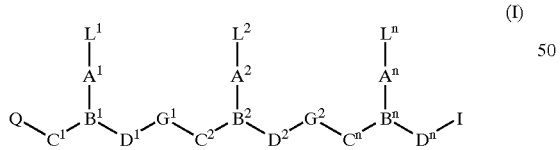

wherein:
n is at least 2,
each of $L^1$–$L^n$ is independently selected from the group consisting of hydrogen, hydroxy, ($C_1$–$C_4$) alkanoyl, naturally occurring nucleobases, non-naturally occurring nucleobases, aromatic moieties, DNA intercalators, nucleobase-binding groups and reporter ligands, at least one of $L^1$–$L^n$ being a naturally occurring nucleobase, a non-naturally occurring nucleobase, a DNA intercalator, or a nucleobase-binding group;
each of $A^1$ through $A^n$ is a single bond, a methylene group or a group of formula (IIa) or (IIb):

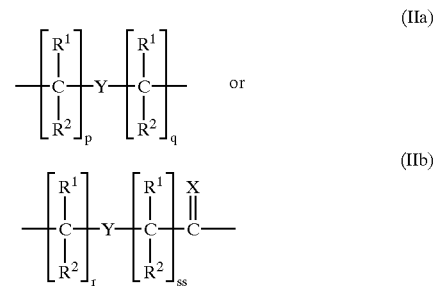

wherein in (IIa) or (IIb):
X is O, S, Se, $NR^3$, $CH_2$ or $C(CH_3)_2$;
Y is a single bond, O, S or $NR^4$;
each of p and q is an integer from 1 to 5, the sum p+q being not more than 10;
each of r and ss is zero or an integer from 1 to 5, the sum r+ss being not more than 10;
each $R^1$ and $R^2$ is independently selected from the group consisting of hydrogen, ($C_1$–$C_4$) alkyl which may be hydroxy- or alkoxy- or alkylthio-substituted, hydroxy, alkoxy, alkylthio, amino and halogen; and
each $R^3$ and $R^4$ is independently selected from the group consisting of hydrogen, ($C_1$–$C_4$) alkyl, hydroxy- or alkoxy- or alkylthio-substituted ($C_1$–$C_4$)alkyl, hydroxy, alkoxy, alkylthio and amino;
and wherein in formula (I);
each of $B^1$–$B^n$ is N or $R^3N^+$, where $R^3$ is as defined above;
each of $C^1$–$C^n$ is $CR^6R^7$, $CHR^6CHR^7$ or $CR^6R^7CH_2$, wherein $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$) alkyl, aryl, aralkyl, heteroaryl, hydroxy, ($C_1$–$C_6$) alkoxy, ($C_1$–$C_6$) alkylthio, $NR^3R^4$ and $SR^5$, where $R^3$ and $R^4$ are as defined above, and $R^5$ is hydrogen, ($C_1$–$C_6$) alkyl, hydroxy-, alkoxy-, or alkylthio- substituted ($C_1$–$C_6$) alkyl, or $R^6$ and $R^7$ taken together complete an alicyclic or heterocyclic system;
each of $D^1$–$D^n$ is $CR^6R^7$, $CH_2CR^6R^7$ or $CHR^6CHR^7$, where $R^6$ and $R^7$ are as defined above;
each of $G^1$–$G^{n-1}$ is

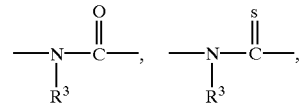

-continued

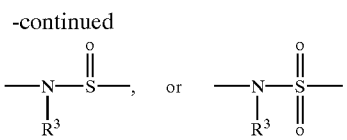

in either orientation, wherein $R^3$ is as defined above;

Q is —$CO_2H$, —$CONR'R''$, —$SO_3H$ or $SO_2NR'R''$ or an activated derivative of —$CO_2H$, —$SO_3H$; and I is —$NHR'''R''''$ or —$NR'''C(O)R''''$, where R', R", R''' and R'''' are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers, wherein C and D can optionally be $CHR^6(CH_2)_{sss}CHR^7$ where sss is from 0 to 2.

26. The method according to claim 25, wherein the conditions under which the nucleic acid to be sequenced binds to the peptide nucleic acid probes include the presence of less than 100 mM salts.

27. The method according to claim 25, wherein the binding of the nucleic acid to the carrier is determined by using an intercalating agent.

28. The method according to claim 25, wherein a detectably labeled antibody to the nucleic acid/peptide nucleic acid binding complex is used to measure the binding of the nucleic acid to the carrier.

29. The method of claim 25, wherein said peptide nucleic acids have the general formula (III):

(III)

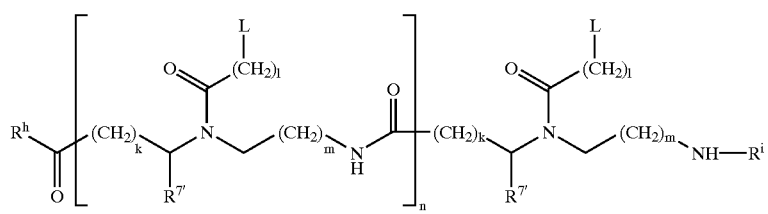

wherein:
each L is independently selected from the group consisting of hydrogen, phenyl, heterocycles, one, two or three rings, naturally occurring nucleobases, and non-naturally occurring nucleobases;

each $R^{7'}$ is independently selected from the group consisting of hydrogen and the side chains of naturally occurring alpha amino acids;

n is an integer from 1 to 60;

each of k, 1 and m is independently zero or an integer from 1 to 5; and optionally the sum of k and m is 1 or 2;

$R^h$ is OH, $NH_2$ or —$NHLysNH_2$; and $R^i$ is H or $COCH_3$.

30. The method of claim 25 wherein the peptide nucleic acids have a backbone of 2aminoethyl-glycine subunits.

31. A method for the quantitative determination of a nucleic acid, said method comprising:

contacting a sample that contains a target nucleic acid to be determined with a solid carrier comprising at least two single stranded peptide nucleic acid probes of different base sequence, each probe being covalently bound to a separate and distinct region of the solid carrier, and wherein at least one peptide nucleic acid probe binds to nucleic acid in said sample under conditions where the target nucleic acid binds to the peptide nucleic acid probe, and wherein at least one of said peptide nucleic acid probes has a base sequence that is complementary to the base sequence of the target nucleic acid, and wherein one additional peptide nucleic acid acid probe has a base sequence that is not complementary to the base sequence of the target nucleic acid, and wherein said target nucleic acid is detectably labeled; and determining the amount of target nucleic acid in said sample by determining the intensity of the detectable label bound in a region of the solid carrier that contains peptide nucleic acid probes having a base sequence that is complementary to the base sequence of the target nucleic acid wherein the probes are nucleic acid analogs that have the general formula (I):

(I)

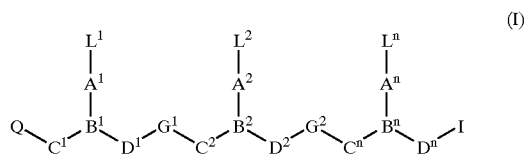

wherein:
n is at least 2, each of $L^1$–$L^n$ is independently selected from the group consisting of hydrogen, hydroxy, ($C_1$–$C_4$) alkanoyl, naturally occurring nucleobases, non-naturally occurring nucleobases, aromatic moieties, DNA intercalators, nucleobase-binding groups and reporter ligands, at least one of $L^1$–$L^n$ being a naturally occurring nucleobase, a non-naturally occurring nucleobase, a DNA intercalator, or a nucleobase-binding group;

each of $A^1$ through $A^n$ is a single bond, a methylene group or a group of formula (IIa) or (IIb):

(IIa)

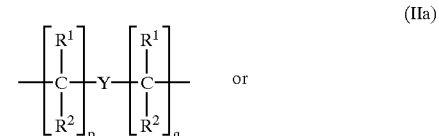

(IIb)

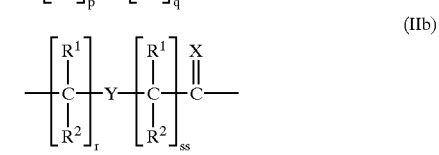

wherein in (IIa) or (IIb):

X is O, S, Se, $NR^3$, $CH_2$ or $C(CH_3)_2$;

Y is a single bond, O, S or NR$^4$;

each of p and q is an integer from 1 to 5, the sum p+q being not more than 10;

each of r and ss is zero or an integer from 1 to 5, the sum r+ss being not more than 10;

each R$^1$ and R$^2$ is independently selected from the group consisting of hydrogen, (C$_1$–C$_4$) alkyl which may be hydroxy- or alkoxy- or alkylthio-substituted, hydroxy, alkoxy, alkylthio, amino and halogen; and each R$^3$ and R$^4$ is independently selected from the group consisting of hydrogen, (C$_1$–C$_4$) alkyl, hydroxy- or alkoxy- or alkylthio-substituted (C$_1$–C$_4$)alkyl, hydroxy, alkoxy, alkylthio and amino;

and wherein in formula (I);

each of B$^1$–B$^n$ is N or R$^3$N$^+$, where R$^3$ is as defined above;

each of C$^1$–C$^n$ is CR$^6$R$^7$, CHR$^6$CHR$^7$ or CR$^6$R$^7$CH$_2$, wherein R$^6$ is hydrogen and R$^7$ is selected from the group consisting of the side chains of naturally occurring alpha amino acids, or R$^6$ and R$^7$ are independently selected from the group consisting of hydrogen, (C$_2$–C$_6$) alkyl, aryl, aralkyl, heteroaryl, hydroxy, (C$_1$–C$_6$) alkoxy, (C$_1$–C$_6$) alkylthio, NR$^3$R$^4$ and SR$^5$, where R$^3$ and R$^4$ are as defined above, and R$^5$ is hydrogen, (C$_1$–C$_6$) alkyl, hydroxy-, alkoxy-, or alkylthio- substituted (C$_1$–C$_6$) alkyl, or R$^6$ and R$^7$ taken together complete an alicyclic or heterocyclic system;

each of D$^1$–D$^n$ is CR$^6$R$^7$, CH$_2$CR$^6$R$^7$ or CHR$^6$CHR$^7$, where R$^6$ and R$^7$ are as defined above;

each of G$^1$–G$^{n-1}$ is

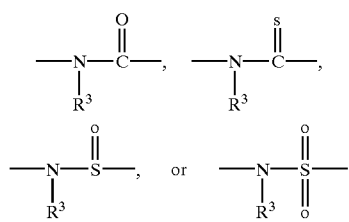

in either orientation, wherein R$^3$ is as defined above;

Q is —CO$_2$H, —CONR'R", —SO$_3$H or SO$_2$NR'R" or an activated derivative of —CO$_2$H, —SO$_3$H; and I is —NHR'''R"" or —NR'''C(O)R"", where R', R", R''' and R"" are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers, wherein C and D can optionally be CHR$^6$(CH$_2$)$_{sss}$CHR$^7$ where sss is from 0 to 2.

32. The method according to claim 31, wherein said target nucleic acid is the product of an amplification reaction.

33. The method according to claim 31, wherein the conditions under which the target nucleic binds to the peptide nucleic acid probe include the presence of less than 100 mM salts.

34. The method of claim 31, wherein said peptide nucleic acids have the general formula (III):

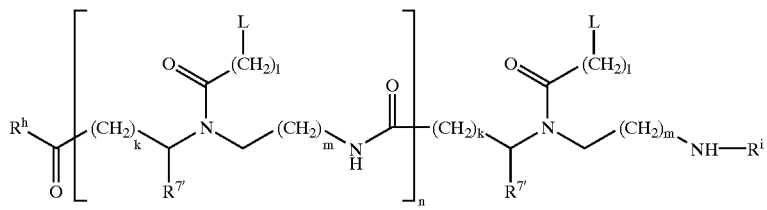

wherein:

each L is independently selected from the group consisting of hydrogen, phenyl, heterocycles, one, two or three rings, naturally occurring nucleobases, and non-naturally occurring nucleobases;

each R$^{7\prime}$ is independently selected from the group consisting of hydrogen and the side chains of naturally occurring alpha amino acids;

n is an integer from 1 to 60;

each of k, l and m is independently zero or an integer from 1 to 5; and optionally the sum of k and m is 1 or 2;

R$^h$ is OH, NH$_2$ or —NHLysNH$_2$; and

R$^i$ is H or COCH$_3$.

35. The method of claim 31 wherein the peptide nucleic acids have a backbone of 2-aminoethyl-glycine subunits.

36. A method for determining the location of two or more different peptide nucleic acid/nucleic acid complexes on a basically planar solid carrier, said method comprising:

treating the carrier with an agent that deposits selectively on the complexes; and determining the location of the agent on said carrier to thereby determine the location of the two or more complexes on said carrier wherein the peptide nucleic acids are nucleic acid analogs that have the general formula (I):

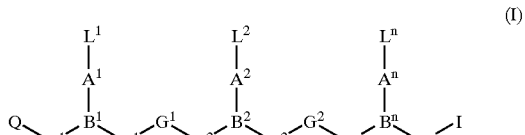

wherein:

n is at least 2, each of L$^1$–L$^n$ is independently selected from the group consisting of hydrogen, hydroxy, (C$_1$–C$_4$) alkanoyl, naturally occurring nucleobases, non-naturally occurring nucleobases, aromatic moieties, DNA intercalators, nucleobase-binding groups and reporter ligands, at least one of L$^1$–L$^n$ being a naturally occurring nucleobase, a non-naturally occurring nucleobase, a DNA intercalator, or a nucleobase-binding group;

each of $A^1$ through $A^n$ is a single bond, a methylene group or a group of formula (IIa) or (IIb):

$$\left[\begin{array}{c} R^1 \\ | \\ -C- \\ | \\ R^2 \end{array}\right]_p Y \left[\begin{array}{c} R^1 \\ | \\ -C- \\ | \\ R^2 \end{array}\right]_q \quad \text{or} \tag{IIa}$$

$$\left[\begin{array}{c} R^1 \\ | \\ -C- \\ | \\ R^2 \end{array}\right]_r Y \left[\begin{array}{c} R^1 \\ | \\ -C- \\ | \\ R^2 \end{array}\right]_{ss} \overset{X}{\underset{}{\overset{\|}{C}}}- \tag{IIb}$$

wherein in (IIa) or (IIb):

X is O, S, Se, $NR^3$, $CH_2$ or $C(CH_3)_2$;

Y is a single bond, O, S or $NR^4$;

each of p and q is an integer from 1 to 5, the sum p+q being not more than 10;

each of r and ss is zero or an integer from 1 to 5, the sum r+ss being not more than 10;

each $R^1$ and $R^2$ is independently selected from the group consisting of hydrogen, $(C_1-C_4)$ alkyl which may be hydroxy- or alkoxy- or alkylthio-substituted, hydroxy, alkoxy, alkylthio, amino and halogen; and each $R^3$ and $R^4$ is independently selected from the group consisting of hydrogen, $(C_1-C_4)$ alkyl, hydroxy- or alkoxy- or alkylthio-substituted $(C_1-C_4)$alkyl, hydroxy, alkoxy, alkylthio and amino;

and wherein in formula (I);

each of $B^1-B^n$ is N or $R^3N^+$, where $R^3$ is as defined above;

each of $C^1-C^n$ is $CR^6R^7$, $CHR^6CHR^7$ or $CR^6R^7CH_2$, wherein $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$ alkyl, aryl, aralkyl, heteroaryl, hydroxy, $(C_1-C_6)$ alkoxy, $(C_1-C_6)$ alkylthio, $NR^3R^4$ and $SR^5$, where $R^3$ and $R^4$ are as defined above, and $R^5$ is hydrogen, $(C_1-C_6)$ alkyl, hydroxy-, alkoxy-, or alkylthio- substituted $(C_1-C_6)$ alkyl, or $R^6$ and $R^7$ taken together complete an alicyclic or heterocyclic system;

each of $D^1-D^n$ is $CR^6R^7$, $CH_2CR^6R^7$ or $CHR^6CHR^7$, where $R^6$ and $R^7$ are as defined above;

each of $G^1-G^{n-1}$ is $$-\underset{\underset{R^3}{|}}{N}-\overset{\overset{O}{\|}}{C}-, \quad -\underset{\underset{R^3}{|}}{N}-\overset{\overset{S}{\|}}{C}-,$$

-continued $$-\underset{\underset{R^3}{|}}{N}-\overset{\overset{O}{\|}}{\underset{\underset{}{\|}}{S}}-, \quad \text{or} \quad -\underset{\underset{R^3}{|}}{N}-\overset{\overset{O}{\|}}{\underset{\underset{O}{\|}}{S}}-$$

in either orientation, wherein $R^3$ is as defined above;

Q is $-CO_2H$, $-CONR'R''$, $-SO_3H$ or $SO_2NR'R''$ or an activated derivative of $-CO_2H$, $-SO_3H$; and I is $-NHR'''R''''$ or $-NR'''C(O)R''''$, where R', R'', R''' and R'''' are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers, wherein C and D can optionally be $CHR^6(CH_2)_{sss}CHR^7$ where sss is from 0 to 2.

37. The method of claim 36, wherein the agent is an intercalating agent.

38. The method of claim 36, wherein the agent is a detectably labeled antibody to the peptide nucleic acid/nucleic acid complex.

39. The method in claim 36, wherein said peptide nucleic acids have the general formula (III):

$$R^h-\overset{\overset{O}{\|}}{C}-(CH_2)_k-\underset{\underset{R^{7'}}{|}}{N}-\overset{\overset{O}{\|}}{\underset{(CH_2)_l}{\underset{|}{L}}} \ldots \left[(CH_2)_m-\overset{}{\underset{H}{N}}-\overset{\overset{O}{\|}}{C}-(CH_2)_k-\underset{\underset{R^{7'}}{|}}{N}-\overset{\overset{O}{\|}}{\underset{(CH_2)_l}{\underset{|}{L}}}\right]_n (CH_2)_m-NH-R^i \tag{III}$$

wherein:

each L is independently selected from the group consisting of hydrogen, phenyl, heterocycles, one, two or three rings, naturally occurring nucleobases, and non-naturally occurring nucleobases;

each $R^{7'}$ is independently selected from the group consisting of hydrogen and the side chains of naturally occurring alpha amino acids;

n is an integer from 1 to 60;

each of k, l and m is independently zero or an integer from 1 to 5; and optionally the sum of k and m is 1 or 2;

$R^h$ is OH, $NH_2$ or $-NHLysNH_2$; and $R^i$ is H or $COCH_3$.

40. The method of claim 36 wherein the peptide nucleic acids have a backbone of 2-aminoethyl-glycine subunits.

41. The method of claim 64, wherein said peptide nucleic acids have the general formula (III):

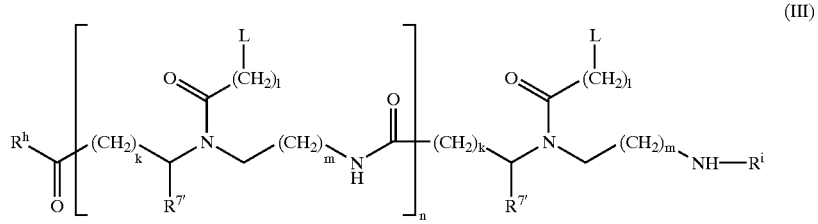

(III)

wherein:

each L is independently selected from the group consisting of hydrogen, phenyl, heterocycles, one, two or three rings, naturally occurring nucleobases, and non-naturally occurring nucleobases;

each $R^{7'}$ is independently selected from the group consisting of hydrogen and the side chains of naturally occurring alpha amino acids;

n is an integer from 1 to 60;

each of k, l and m is independently zero or an integer from 1 to 5; and optionally the sum of k and m is 1 or 2;

$R^h$ is OH, $NH_2$ or —$NHLysNH_2$; and $R^i$ is H or $COCH_3$.

* * * * *

SEQUENCE LISTING

<160> NUMBER OF SEQ ID NOS: 13

<210> SEQ ID NO 1
<211> LENGTH: 16
<212> TYPE: PRT
<213> ORGANISM: Unknown
<220> FEATURE:
<223> OTHER INFORMATION: Description of Unknown Organism: Synthetic
<221> NAME/KEY: misc_feature
<222> LOCATION: (15)
<223> OTHER INFORMATION: note= "Xaa is N-((1-adeninyl)acetyl)-N-(2-aminoethyl)-beta-alanine"
<221> NAME/KEY: misc_feature
<222> LOCATION: (14)
<223> OTHER INFORMATION: note= "Xaa is N-((1-thyminyl)acetyl)-N-(2-aminoethyl)-beta-alanine"
<221> NAME/KEY: misc_feature
<222> LOCATION: (13)
<223> OTHER INFORMATION: note= "Xaa is N-((1-cytosyl)acetyl)-N-(2-aminoethyl)-beta-alanine"
<221> NAME/KEY: misc_feature
<222> LOCATION: (11)..(12)
<223> OTHER INFORMATION: note= "Xaa is N-((1-adeninyl)acetyl)-N-(2-aminoethyl)-beta-alanine"
<221> NAME/KEY: misc_feature
<222> LOCATION: (10)
<223> OTHER INFORMATION: note= "Xaa is N-((1-cytosyl)acetyl)-N-(2-aminoethyl)-beta-alanine"
<221> NAME/KEY: misc_feature
<222> LOCATION: (9)
<223> OTHER INFORMATION: note= "Xaa is N-((1-adeninyl)acetyl)-N-(2-aminoethyl)-beta-alanine"
<221> NAME/KEY: misc_feature
<222> LOCATION: (8)
<223> OTHER INFORMATION: note= "Xaa is N-((1-cytosyl)acetyl)-N-(2-aminoethyl)-beta-alanine"
<221> NAME/KEY: misc_feature
<222> LOCATION: (7)
<223> OTHER INFORMATION: note= "Xaa is N-((1-thyminyl)acetyl)-N-(2-aminoethyl)-beta-alanine"
<221> NAME/KEY: misc_feature
<222> LOCATION: (6)
<223> OTHER INFORMATION: note= "Xaa is N-((1-guaninyl)acetyl)-N-(2-aminoethyl)-beta-alanine"
<221> NAME/KEY: misc_feature
<222> LOCATION: (5)
<223> OTHER INFORMATION: note= "Xaa is N-((1-cytosyl)acetyl)-N-(2-aminoethyl)-beta-alanine"
<221> NAME/KEY: misc_feature
<222> LOCATION: (4)
<223> OTHER INFORMATION: note= "Xaa is N-((1-adeninyl)acetyl)-N-(2-

```
       aminoethyl)-beta-alanine"
<221> NAME/KEY: misc_feature
<222> LOCATION: (3)
<223> OTHER INFORMATION: note= "Xaa is N-((1-thyminyl)acetyl)-N-(2-
       aminoethyl)-beta-alanine"
<221> NAME/KEY: misc_feature
<222> LOCATION: (2)
<223> OTHER INFORMATION: note= "Xaa is N-((1-guaninyl)acetyl)-N-(2-
       aminoethyl)-beta-alanine"
<221> NAME/KEY: misc_feature
<222> LOCATION: (1)
<223> OTHER INFORMATION: note= "Xaa is N-((1-thyminyl)acetyl)-N-(2-
       amino-N'-(hexa(8-amino-3,6-dioxa-octano-1-yl)-ethyl)-beta-alanine"
<221> NAME/KEY: misc_feature
<222> LOCATION: (16)
<223> OTHER INFORMATION: Product= "OTHER" note="Amide"

<400> SEQUENCE: 1

Xaa Xaa Xaa Xaa Xaa Xaa Xaa Xaa Xaa Xaa Xaa Xaa Xaa Xaa Xaa Gly
 1               5                  10                  15

<210> SEQ ID NO 2
<211> LENGTH: 16
<212> TYPE: PRT
<213> ORGANISM: Unknown
<220> FEATURE:
<223> OTHER INFORMATION: Description of Unknown Organism: Synthetic
<221> NAME/KEY: misc_feature
<222> LOCATION: (15)
<223> OTHER INFORMATION: note= "Xaa is N-((1-adeninyl)acetyl)-N-(2-
       aminoethyl)-beta-alanine"
<221> NAME/KEY: misc_feature
<222> LOCATION: (14)
<223> OTHER INFORMATION: note= "Xaa is N-((1-thyminyl)acetyl)-N-(2-
       aminoethyl)-beta-alanine"
<221> NAME/KEY: misc_feature
<222> LOCATION: (13)
<223> OTHER INFORMATION: note= "Xaa is N-((1-cytosyl)acetyl)-N-(2-
       aminoethyl)-beta-alanine"
<221> NAME/KEY: misc_feature
<222> LOCATION: (11)..(12)
<223> OTHER INFORMATION: note= "Xaa is N-((1-adeninyl)acetyl)-N-(2-
       aminoethyl)-beta-alanine"
<221> NAME/KEY: misc_feature
<222> LOCATION: (10)
<223> OTHER INFORMATION: note= "Xaa is N-((1-cytosyl)acetyl)-N-(2-
       aminoethyl)-beta-alanine"
<221> NAME/KEY: misc_feature
<222> LOCATION: (9)
<223> OTHER INFORMATION: note= "Xaa is N-((1-adeninyl)acetyl)-N-(2-
       aminoethyl)-beta-alanine"
<221> NAME/KEY: misc_feature
<222> LOCATION: (8)
<223> OTHER INFORMATION: note= "Xaa is N-((1-guaninyl)acetyl)-N-(2-
       aminoethyl)-beta-alanine"
<221> NAME/KEY: misc_feature
<222> LOCATION: (7)
<223> OTHER INFORMATION: note= "Xaa is N-((1-thyminyl)acetyl)-N-(2-
       aminoethyl)-beta-alanine"
<221> NAME/KEY: misc_feature
<222> LOCATION: (6)
<223> OTHER INFORMATION: note= "Xaa is N-((1-guaninyl)acetyl)-N-(2-
       aminoethyl)-beta-alanine"
<221> NAME/KEY: misc_feature
<222> LOCATION: (5)
<223> OTHER INFORMATION: note= "Xaa is N-((1-cytosyl)acetyl)-N-(2-
       aminoethyl)-beta-alanine"
<221> NAME/KEY: misc_feature
<222> LOCATION: (4)
<223> OTHER INFORMATION: note= "Xaa is N-((1-adeninyl)acetyl)-N-(2-
       aminoethyl)-beta-alanine"
<221> NAME/KEY: misc_feature
<222> LOCATION: (3)
<223> OTHER INFORMATION: note= "Xaa is N-((1-thyminyl)acetyl)-N-(2-
       aminoethyl)-beta-alanine"
<221> NAME/KEY: misc_feature
<222> LOCATION: (2)
```

<223> OTHER INFORMATION: note= "Xaa is N-((1-guaninyl)acetyl)-N-(2-
       aminoethyl)-beta-alanine"
<221> NAME/KEY: misc_feature
<222> LOCATION: (1)
<223> OTHER INFORMATION: note= "Xaa is
       N-((1-thyminyl)acetyl)-N-(2-amino-N'-(hexa(8-amino-3,6-dioxa-
       octano-1-yl)-ethyl)-beta-alanine"
<221> NAME/KEY: misc_feature
<222> LOCATION: (16)
<223> OTHER INFORMATION: Product= "OTHER" note="Amide"

<400> SEQUENCE: 2

Xaa Xaa Xaa Xaa Xaa Xaa Xaa Xaa Xaa Xaa Xaa Xaa Xaa Xaa Xaa Gly
 1               5                   10                  15

<210> SEQ ID NO 3
<211> LENGTH: 16
<212> TYPE: PRT
<213> ORGANISM: Unknown
<220> FEATURE:
<223> OTHER INFORMATION: Description of Unknown Organism: Synthetic
<221> NAME/KEY: misc_feature
<222> LOCATION: (15)
<223> OTHER INFORMATION: note= "Xaa is N-((1-adeninyl)acetyl)-N-(2-
       aminoethyl)-beta-alanine"
<221> NAME/KEY: misc_feature
<222> LOCATION: (14)
<223> OTHER INFORMATION: note= "Xaa is N-((1-thyminyl)acetyl)-N-(2-
       aminoethyl)-beta-alanine"
<221> NAME/KEY: misc_feature
<222> LOCATION: (13)
<223> OTHER INFORMATION: note= "Xaa is N-((1-cytosyl)acetyl)-N-(2-
       aminoethyl)-beta-alanine"
<221> NAME/KEY: misc_feature
<222> LOCATION: (11)..(12)
<223> OTHER INFORMATION: note= "Xaa is N-((1-adeninyl)acetyl)-N-(2-
       aminoethyl)-beta-alanine"
<221> NAME/KEY: misc_feature
<222> LOCATION: (10)
<223> OTHER INFORMATION: note= "Xaa is N-((1-cytosyl)acetyl)-N-(2-
       aminoethyl)-beta-alanine"
<221> NAME/KEY: misc_feature
<222> LOCATION: (9)
<223> OTHER INFORMATION: note= "Xaa is N-((1-adeninyl)acetyl)-N-(2-
       aminoethyl)-beta-alanine"
<221> NAME/KEY: misc_feature
<222> LOCATION: (8)
<223> OTHER INFORMATION: note= "Xaa is N-((1-cytosyl)acetyl)-N-(2-
       aminoethyl)-beta-alanine"
<221> NAME/KEY: misc_feature
<222> LOCATION: (7)
<223> OTHER INFORMATION: note= "Xaa is N-((1-thyminyl)acetyl)-N-(2-
       aminoethyl)-beta-alanine"
<221> NAME/KEY: misc_feature
<222> LOCATION: (6)
<223> OTHER INFORMATION: note= "Xaa is N-((1-adeninyl)acetyl)-N-(2-
       aminoethyl)-beta-alanine"
<221> NAME/KEY: misc_feature
<222> LOCATION: (5)
<223> OTHER INFORMATION: note= "Xaa is N-((1-cytosyl)acetyl)-N-(2-
       aminoethyl)-beta-alanine"
<221> NAME/KEY: misc_feature
<222> LOCATION: (4)
<223> OTHER INFORMATION: note= "Xaa is N-((1-adeninyl)acetyl)-N-(2-
       aminoethyl)-beta-alanine"
<221> NAME/KEY: misc_feature
<222> LOCATION: (3)
<223> OTHER INFORMATION: note= "Xaa is N-((1-thyminyl)acetyl)-N-(2-
       aminoethyl)-beta-alanine"
<221> NAME/KEY: misc_feature
<222> LOCATION: (2)
<223> OTHER INFORMATION: note= "Xaa is N-((1-guaninyl)acetyl)-N-(2-
       aminoethyl)-beta-alanine"
<221> NAME/KEY: misc_feature
<222> LOCATION: (1)
<223> OTHER INFORMATION: note= "Xaa is
       N-((1-thyminyl)acetyl)-N-(2-amino-N'-(hexa(8-amino-3,6-dioxaoctano-1-yl)-ethyl)-beta-alanine"
<221> NAME/KEY: misc_feature
<222> LOCATION: (16)
<223> OTHER INFORMATION: Product= "OTHER" note="Amide"

<400> SEQUENCE: 3

Xaa Xaa Xaa Xaa Xaa Xaa Xaa Xaa Xaa Xaa Xaa Xaa Xaa Xaa Xaa Gly
 1               5                   10                  15

<210> SEQ ID NO 4
<211> LENGTH: 15
<212> TYPE: DNA
<213> ORGANISM: Unknown
<220> FEATURE:
<223> OTHER INFORMATION: Description of Unknown Organism: Synthetic
<223> OTHER INFORMATION: Molecule Type: Other nucleic acid=
      "oligodesoxyribonucleotide"
<221> NAME/KEY: misc_feature
<222> LOCATION: (15)
<223> OTHER INFORMATION: note= "labelled at the 5'-phosphate with
      digoxigenin via aminolinker (Boehringer Mannheim GmbH, BRD) or
      32-P"

<400> SEQUENCE: 4
tagttgtgac gtaca                                                    15

<210> SEQ ID NO 5
<211> LENGTH: 15
<212> TYPE: DNA
<213> ORGANISM: Unknown
<220> FEATURE:
<223> OTHER INFORMATION: Description of Unknown Organism: Synthetic
<223> OTHER INFORMATION: Molecule Type: Other nucleic acid=
      "oligodesoxyribonucleotide"
<221> NAME/KEY: misc_feature
<222> LOCATION: (15)
<223> OTHER INFORMATION: note= "labelled at the 5'-phosphate with
      digoxigenin via aminolinker (Boehringer Mannheim GmbH, BRD)"

<400> SEQUENCE: 5
tagttgtcac gtaca                                                    15

<210> SEQ ID NO 6
<211> LENGTH: 15
<212> TYPE: DNA
<213> ORGANISM: Unknown
<220> FEATURE:
<223> OTHER INFORMATION: Description of Unknown Organism: Synthetic
<223> OTHER INFORMATION: Molecule Type: Other nucleic acid=
      "oligodesoxyribonucleotide"
<221> NAME/KEY: misc_feature
<222> LOCATION: (15)
<223> OTHER INFORMATION: note= "labelled at the 5'-phosphate with
      digoxigenin via aminolinker (Boehringer Mannheim GmbH, BRD)"

<400> SEQUENCE: 6
tagttgtgat gtaca                                                    15

<210> SEQ ID NO 7
<211> LENGTH: 16
<212> TYPE: PRT
<213> ORGANISM: Unknown
<220> FEATURE:
<223> OTHER INFORMATION: Description of Unknown Organism: Synthetic
<221> NAME/KEY: misc_feature
<222> LOCATION: (15)
<223> OTHER INFORMATION: note= "Xaa is N-((1-adeninyl)acetyl)-N-(2-
      aminoethyl)-beta-alanine"
<221> NAME/KEY: misc_feature
<222> LOCATION: (14)
<223> OTHER INFORMATION: note= "Xaa is N-((1-thyminyl)acetyl)-N-(2-

```
aminoethyl)-beta-alanine"
<221> NAME/KEY: misc_feature
<222> LOCATION: (13)
<223> OTHER INFORMATION: note= "Xaa is N-((1-cytosyl)acetyl)-N-(2-
      aminoethyl)-beta-alanine"
<221> NAME/KEY: misc_feature
<222> LOCATION: (11)..(12)
<223> OTHER INFORMATION: note= "Xaa is N-((1-adeninyl)acetyl)-N-(2-
      aminoethyl)-beta-alanine"
<221> NAME/KEY: misc_feature
<222> LOCATION: (10)
<223> OTHER INFORMATION: note= "Xaa is N-((1-cytosyl)acetyl)-N-(2-
      aminoethyl)-beta-alanine"
<221> NAME/KEY: misc_feature
<222> LOCATION: (9)
<223> OTHER INFORMATION: note= "Xaa is N-((1-adeninyl)acetyl)-N-(2-
      aminoethyl)-beta-alanine"
<221> NAME/KEY: misc_feature
<222> LOCATION: (8)
<223> OTHER INFORMATION: note= "Xaa is N-((1-cytosyl)acetyl)-N-(2-
      aminoethyl)-beta-alanine"
<221> NAME/KEY: misc_feature
<222> LOCATION: (7)
<223> OTHER INFORMATION: note= "Xaa is N-((1-thyminyl)acetyl)-N-(2-
      aminoethyl)-beta-alanine"
<221> NAME/KEY: misc_feature
<222> LOCATION: (6)
<223> OTHER INFORMATION: note= "Xaa is N-((1-guaninyl)acetyl)-N-(2-
      aminoethyl)-beta-alanine"
<221> NAME/KEY: misc_feature
<222> LOCATION: (5)
<223> OTHER INFORMATION: note= "Xaa is N-((1-cytosyl)acetyl)-N-(2-
      aminoethyl)-beta-alanine"
<221> NAME/KEY: misc_feature
<222> LOCATION: (4)
<223> OTHER INFORMATION: note= "Xaa is N-((1-adeninyl)acetyl)-N-(2-
      aminoethyl)-beta-alanine"
<221> NAME/KEY: misc_feature
<222> LOCATION: (3)
<223> OTHER INFORMATION: note= "Xaa is N-((1-thyminyl)acetyl)-N-(2-
      aminoethyl)-beta-alanine"
<221> NAME/KEY: misc_feature
<222> LOCATION: (2)
<223> OTHER INFORMATION: note= "Xaa is N-((1-guaninyl)acetyl)-N-(2-
      aminoethyl)-beta-alanine"
<221> NAME/KEY: misc_feature
<222> LOCATION: (1)
<223> OTHER INFORMATION: note= "Xaa is
      N-((1-thyminyl)acetyl)-N-(2-amino-N'-(tri(8-amino-3,6-dioxa-
      octano-1-yl)-ethyl)-beta-alanine"
<221> NAME/KEY: misc_feature
<222> LOCATION: (16)
<223> OTHER INFORMATION: Product= "OTHER" note="Amide"

<400> SEQUENCE: 7

Xaa Xaa Xaa Xaa Xaa Xaa Xaa Xaa Xaa Xaa Xaa Xaa Xaa Xaa Xaa Gly
  1               5                  10                  15

<210> SEQ ID NO 8
<211> LENGTH: 30
<212> TYPE: DNA
<213> ORGANISM: Unknown
<220> FEATURE:
<223> OTHER INFORMATION: Description of Unknown Organism: Synthetic
<223> OTHER INFORMATION: Molecule Type: Other nucleic acid=
      "oligodesoxyribonucleotide"

<400> SEQUENCE: 8
tttttttttt tttttttgtac gtcacaacta                                    30

<210> SEQ ID NO 9
<211> LENGTH: 16
<212> TYPE: PRT
<213> ORGANISM: Unknown
<220> FEATURE:
```

```
<223> OTHER INFORMATION: Description of Unknown Organism: Synthetic
<221> NAME/KEY: misc_feature
<222> LOCATION: (15)
<223> OTHER INFORMATION: note= "Xaa is N-((1-adeninyl)acetyl)-N-(2-
      aminoethyl)-beta-alanine"
<221> NAME/KEY: misc_feature
<222> LOCATION: (14)
<223> OTHER INFORMATION: note= "Xaa is N-((1-thyminyl)acetyl)-N-(2-
      aminoethyl)-beta-alanine"
<221> NAME/KEY: misc_feature
<222> LOCATION: (13)
<223> OTHER INFORMATION: note= "Xaa is N-((1-cytosyl)acetyl)-N-(2-
      aminoethyl)-beta-alanine"
<221> NAME/KEY: misc_feature
<222> LOCATION: (11)..(12)
<223> OTHER INFORMATION: note= "Xaa is N-((1-adeninyl)acetyl)-N-(2-
      aminoethyl)-beta-alanine"
<221> NAME/KEY: misc_feature
<222> LOCATION: (10)
<223> OTHER INFORMATION: note= "Xaa is N-((1-cytosyl)acetyl)-N-(2-
      aminoethyl)-beta-alanine"
<221> NAME/KEY: misc_feature
<222> LOCATION: (9)
<223> OTHER INFORMATION: note= "Xaa is N-((1-adeninyl)acetyl)-N-(2-
      aminoethyl)-beta-alanine"
<221> NAME/KEY: misc_feature
<222> LOCATION: (8)
<223> OTHER INFORMATION: note= "Xaa is N-((1-cytosyl)acetyl)-N-(2-
      aminoethyl)-beta-alanine"
<221> NAME/KEY: misc_feature
<222> LOCATION: (7)
<223> OTHER INFORMATION: note= "Xaa is N-((1-thyminyl)acetyl)-N-(2-
      aminoethyl)-beta-alanine"
<221> NAME/KEY: misc_feature
<222> LOCATION: (6)
<223> OTHER INFORMATION: note= "Xaa is N-((1-guaninyl)acetyl)-N-(2-
      aminoethyl)-beta-alanine"
<221> NAME/KEY: misc_feature
<222> LOCATION: (5)
<223> OTHER INFORMATION: note= "Xaa is N-((1-cytosyl)acetyl)-N-(2-
      aminoethyl)-beta-alanine"
<221> NAME/KEY: misc_feature
<222> LOCATION: (4)
<223> OTHER INFORMATION: note= "Xaa is N-((1-adeninyl)acetyl)-N-(2-
      aminoethyl)-beta-alanine"
<221> NAME/KEY: misc_feature
<222> LOCATION: (3)
<223> OTHER INFORMATION: note= "Xaa is N-((1-thyminyl)acetyl)-N-(2-
      aminoethyl)-beta-alanine"
<221> NAME/KEY: misc_feature
<222> LOCATION: (2)
<223> OTHER INFORMATION: note= "Xaa is N-((1-guaninyl)acetyl)-N-(2-
      aminoethyl)-beta-alanine"
<221> NAME/KEY: misc_feature
<222> LOCATION: (1)
<223> OTHER INFORMATION: note= "Xaa is
      N-((1-thyminyl)acetyl)-N-(2-amino-N'-(nona(8-amino-3,6-dioxa-
      octano-1-yl)-ethyl)-beta-alanine"
<221> NAME/KEY: misc_feature
<222> LOCATION: (16)
<223> OTHER INFORMATION: Product= "OTHER" note="Amide"

<400> SEQUENCE: 9

Xaa Xaa Xaa Xaa Xaa Xaa Xaa Xaa Xaa Xaa Xaa Xaa Xaa Xaa Xaa Gly
 1               5                  10                  15

<210> SEQ ID NO 10
<211> LENGTH: 30
<212> TYPE: DNA
<213> ORGANISM: Unknown
<220> FEATURE:
<223> OTHER INFORMATION: Description of Unknown Organism: Synthetic
<223> OTHER INFORMATION: Molecule Type: Other nucleic acid=
      "oligodesoxyribonucleotide"

<400> SEQUENCE: 10
```

```
ttttttttt tttttgtac gtgacaacta                                    30

<210> SEQ ID NO 11
<211> LENGTH: 30
<212> TYPE: DNA
<213> ORGANISM: Unknown
<220> FEATURE:
<223> OTHER INFORMATION: Description of Unknown Organism: Synthetic
<223> OTHER INFORMATION: Molecule Type: Other nucleic acid=
      "oligodesoxyribonucleotide"

<400> SEQUENCE: 11 ttttttttt tttttgtac atcacaacta                                    30

<210> SEQ ID NO 12
<211> LENGTH: 17
<212> TYPE: DNA
<213> ORGANISM: Unknown
<220> FEATURE:
<223> OTHER INFORMATION: Description of Unknown Organism: Synthetic
<223> OTHER INFORMATION: Molecule Type: Other nucleic acid=
      "oligodesoxyribonucleotide"

<400> SEQUENCE: 12
gtaaaacgac ggccagt                                                17

<210> SEQ ID NO 13
<211> LENGTH: 17
<212> TYPE: DNA
<213> ORGANISM: Unknown
<220> FEATURE:
<223> OTHER INFORMATION: Description of Unknown Organism: Synthetic
<223> OTHER INFORMATION: Molecule Type: Other nucleic acid=
      "oligodesoxyribonucleotide"
<221> NAME/KEY: misc_feature
<222> LOCATION: (15)
<223> OTHER INFORMATION: note=  "A at the 5'-terminus is bound via
      aminomodifier (Boehringer Mannheim GmbH) to digoxigenin''

<400> SEQUENCE: 13
aacagctatg accatga                                                17
```